US008506498B2

(12) United States Patent
Sethi et al.

(10) Patent No.: US 8,506,498 B2
(45) Date of Patent: Aug. 13, 2013

(54) SYSTEMS AND METHODS USING INDUCED PERTURBATION TO DETERMINE PHYSIOLOGICAL PARAMETERS

(75) Inventors: Rakesh Sethi, Vancouver (CA); Paul Stanley Addison, Edinburgh (GB); James Nicholas Watson, Dunfermline (GB)

(73) Assignee: Nellcor Puritan Bennett Ireland, Galway (IE)

( * ) Notice: Subject to any disclaimer, the term of this patent is extended or adjusted under 35 U.S.C. 154(b) by 1086 days.

(21) Appl. No.: 12/248,738

(22) Filed: Oct. 9, 2008

(65) Prior Publication Data

US 2010/0016734 A1 Jan. 21, 2010

Related U.S. Application Data

(60) Provisional application No. 61/080,953, filed on Jul. 15, 2008.

(51) Int. Cl.
*A61B 5/02* (2006.01)
*G06F 19/00* (2011.01)

(52) U.S. Cl.
USPC ............................................ 600/501; 702/19

(58) Field of Classification Search
None
See application file for complete search history.

(56) References Cited

U.S. PATENT DOCUMENTS

| | | |
|---|---|---|
| 3,835,840 A | 9/1974 | Mount |
| 4,289,141 A | 9/1981 | Cormier |
| 4,561,447 A | 12/1985 | Kawamura et al. |
| 4,676,253 A | 6/1987 | Newman |
| 4,729,382 A | 3/1988 | Schaffer |
| 4,830,017 A | 5/1989 | Perry |
| 4,836,213 A | 6/1989 | Wenzel et al. |
| 4,854,327 A | 8/1989 | Kunig |
| 4,898,176 A | 2/1990 | Petre |
| 4,924,871 A | 5/1990 | Honeyager |
| 4,928,700 A | 5/1990 | Harada |
| 4,951,679 A | 8/1990 | Harada |
| 4,976,268 A | 12/1990 | Kurosawa et al. |
| 4,987,900 A | 1/1991 | Eckerle |
| 5,065,765 A | 11/1991 | Eckerle |
| 5,103,831 A | 4/1992 | Niwa |
| 5,105,815 A | 4/1992 | Hall et al. |
| 5,119,824 A | 6/1992 | Niwa |
| 5,131,400 A | 7/1992 | Harada |
| 5,163,328 A | 11/1992 | Holland |
| 5,170,796 A | 12/1992 | Kobayashi |
| 5,176,143 A | 1/1993 | Eckerle et al. |
| 5,178,154 A | 1/1993 | Ackmann et al. |
| 5,179,956 A | 1/1993 | Harada et al. |
| 5,204,922 A | 4/1993 | Weir |
| 5,238,000 A | 8/1993 | Niwa |
| 5,241,964 A | 9/1993 | McQuilkin |
| 5,255,686 A | 10/1993 | Takeda et al. |
| 5,269,312 A | 12/1993 | Kawamura et al. |
| 5,289,823 A | 3/1994 | Eckerle |
| 5,309,917 A | 5/1994 | Wang |
| 5,431,159 A | 7/1995 | Baker |
| 5,439,483 A | 8/1995 | Duong-Van |
| 5,450,852 A | 9/1995 | Archibald et al. |
| 5,467,771 A | 11/1995 | Narimatsu |
| 5,490,506 A | 2/1996 | Takatani |
| 5,494,043 A | 2/1996 | O'Sullivan et al. |
| 5,497,779 A | 3/1996 | Takaya |
| 5,505,209 A | 4/1996 | Reining |
| 5,533,511 A | 7/1996 | Kaspari |
| 5,535,753 A | 7/1996 | Petrucelli et al. |
| 5,562,621 A | 10/1996 | Claude et al. |
| 5,564,427 A | 10/1996 | Aso et al. |
| 5,575,284 A | 11/1996 | Athan |
| 5,590,650 A | 1/1997 | Genova |
| 5,617,868 A | 4/1997 | Harada |
| 5,632,272 A | 5/1997 | Diab et al. |
| 5,640,964 A | 6/1997 | Archibald et al. |
| 5,649,542 A | 7/1997 | Archibald et al. |
| 5,649,543 A | 7/1997 | Hosaka et al. |
| 5,676,140 A | 10/1997 | Ukawa |
| 5,682,898 A | 11/1997 | Aung |
| 5,685,316 A | 11/1997 | Schookin et al. |
| 5,704,362 A | 1/1998 | Hersh et al. |
| 5,709,212 A | 1/1998 | Sugo |
| 5,720,292 A | 2/1998 | Poliac |

(Continued)

FOREIGN PATENT DOCUMENTS

| | | |
|---|---|---|
| EP | 0443267 | 8/1991 |
| GB | 2 356 250 | 5/2001 |

(Continued)

OTHER PUBLICATIONS

Addison, Paul S., The Illustrated Wavelet Transform Handbook, Taylor & Francis Group, 2002.

Addison, Paul, "The Little Wave with the Big Future," Physics World, Mar. 2004, pp. 35-39.

(Continued)

*Primary Examiner* — Lori A Clow

(57) ABSTRACT

According to embodiments, systems and methods for non-invasive blood pressure monitoring are disclosed. An exciter may induce perturbations in a subject, and a sensor or probe may be used to obtain a detected signal from the subject. The detected signal may then be used to measure one or more physiological parameters of the patient. For example if the perturbations are based on a known signal, any differences between the known signal and the input signal may be attributable to the patient's physiological parameters. A phase drift between the perturbation signal and the detected signal may be determined from a comparison of the scalograms of the exciter location and the sensor or probe location. From the scalogram comparison, more accurate and reliable physiological parameters may be determined.

23 Claims, 10 Drawing Sheets

(56) References Cited

U.S. PATENT DOCUMENTS

| | | | |
|---|---|---|---|
| 5,722,414 | A | 3/1998 | Archibald et al. |
| 5,738,103 | A | 4/1998 | Poliac |
| 5,743,856 | A | 4/1998 | Oka et al. |
| 5,755,669 | A | 5/1998 | Ono et al. |
| 5,762,610 | A | 6/1998 | Narimatsu |
| 5,772,601 | A | 6/1998 | Oka |
| 5,772,602 | A | 6/1998 | Sakai |
| 5,776,071 | A | 7/1998 | Inukai |
| 5,778,881 | A | 7/1998 | Sun et al. |
| 5,785,659 | A | 7/1998 | Caro et al. |
| 5,791,347 | A | 8/1998 | Flaherty et al. |
| 5,795,304 | A | 8/1998 | Sun et al. |
| 5,797,395 | A | 8/1998 | Martin |
| 5,797,840 | A | 8/1998 | Akselrod |
| 5,797,850 | A | 8/1998 | Archibald et al. |
| 5,810,736 | A | 9/1998 | Pail |
| 5,827,181 | A | 10/1998 | Dias |
| 5,827,195 | A | 10/1998 | Lander |
| 5,830,131 | A | 11/1998 | Caro et al. |
| 5,832,924 | A | 11/1998 | Archibald et al. |
| 5,833,618 | A | 11/1998 | Caro |
| 5,848,970 | A | 12/1998 | Voss |
| 5,857,975 | A | 1/1999 | Golub |
| 5,873,834 | A | 2/1999 | Yanagi et al. |
| 5,904,654 | A | 5/1999 | Wohltmann et al. |
| 5,941,828 | A | 8/1999 | Archibald et al. |
| 5,964,711 | A | 10/1999 | Voss |
| 5,967,995 | A | 10/1999 | Shusterman et al. |
| 6,002,952 | A | 12/1999 | Diab |
| 6,004,274 | A | 12/1999 | Nolan |
| 6,007,492 | A | 12/1999 | Goto et al. |
| 6,011,986 | A | 1/2000 | Diab et al. |
| 6,022,320 | A | 2/2000 | Ogura |
| 6,027,452 | A | 2/2000 | Flaherty et al. |
| 6,027,453 | A | 2/2000 | Miwa |
| 6,027,455 | A | 2/2000 | Inukai et al. |
| 6,036,653 | A | 3/2000 | Baba et al. |
| 6,045,509 | A | 4/2000 | Caro et al. |
| 6,067,462 | A | 5/2000 | Diab |
| 6,083,171 | A | 7/2000 | Ono et al. |
| 6,094,592 | A | 7/2000 | Yorkey |
| 6,095,984 | A | 8/2000 | Amano et al. |
| 6,095,987 | A | 8/2000 | Shmulewitz |
| 6,117,075 | A | 9/2000 | Barnea |
| 6,129,675 | A | 10/2000 | Jay |
| 6,135,966 | A | 10/2000 | Ko |
| 6,157,850 | A | 12/2000 | Diab et al. |
| 6,159,157 | A | 12/2000 | Archibald et al. |
| 6,161,038 | A | 12/2000 | Schookin et al. |
| 6,171,257 | B1 | 1/2001 | Weil et al. |
| 6,171,258 | B1 | 1/2001 | Karakasoglu et al. |
| 6,186,954 | B1 | 2/2001 | Narimatsu |
| 6,186,955 | B1 | 2/2001 | Baura |
| 6,190,382 | B1 | 2/2001 | Ormsby et al. |
| 6,196,974 | B1 | 3/2001 | Miwa |
| 6,208,951 | B1 | 3/2001 | Kumar et al. |
| 6,217,524 | B1 | 4/2001 | Orr et al. |
| 6,227,196 | B1 | 5/2001 | Jaffe et al. |
| 6,228,034 | B1 | 5/2001 | Voss et al. |
| 6,241,661 | B1 | 6/2001 | Schluess et al. |
| 6,241,679 | B1 | 6/2001 | Curran |
| 6,245,022 | B1 | 6/2001 | Archibald et al. |
| 6,251,081 | B1 | 6/2001 | Narimatsu |
| 6,263,222 | B1 | 7/2001 | Diab et al. |
| 6,292,689 | B1 | 9/2001 | Wallace |
| 6,293,915 | B1 | 9/2001 | Amano et al. |
| 6,299,582 | B1 | 10/2001 | Brockway et al. |
| 6,325,761 | B1 | 12/2001 | Jay |
| 6,332,867 | B1 | 12/2001 | Chen et al. |
| 6,350,242 | B1 | 2/2002 | Doten et al. |
| 6,361,501 | B1 | 3/2002 | Amano et al. |
| 6,371,921 | B1 | 4/2002 | Caro |
| 6,393,311 | B1 | 5/2002 | Edgar, Jr. et al. |
| 6,443,905 | B1 | 9/2002 | Nissila et al. |
| 6,463,311 | B1 | 10/2002 | Diab |
| 6,471,646 | B1 | 10/2002 | Thede |
| 6,471,655 | B1 | 10/2002 | Baura |
| 6,506,161 | B2 | 1/2003 | Brockway et al. |
| 6,514,211 | B1 | 2/2003 | Baura |
| 6,524,240 | B1 | 2/2003 | Thede |
| 6,561,986 | B2 | 5/2003 | Baura |
| 6,589,185 | B1 | 7/2003 | Archibald et al. |
| 6,599,251 | B2 | 7/2003 | Chen et al. |
| 6,602,199 | B2 | 8/2003 | Chen et al. |
| 6,602,201 | B1 | 8/2003 | Hepp et al. |
| 6,606,511 | B1 | 8/2003 | Ali et al. |
| 6,608,934 | B2 | 8/2003 | Scheirer |
| 6,626,839 | B2 | 9/2003 | Doten et al. |
| 6,631,281 | B1 | 10/2003 | Kastle |
| 6,645,156 | B2 | 11/2003 | Oka |
| 6,654,623 | B1 | 11/2003 | Kastle |
| 6,658,277 | B2 | 12/2003 | Wasserman |
| 6,684,090 | B2 | 1/2004 | Ali et al. |
| RE38,476 | E | 3/2004 | Diab et al. |
| 6,699,194 | B1 | 3/2004 | Diab |
| 6,767,328 | B2 | 7/2004 | Kulik |
| 6,773,397 | B2 | 8/2004 | Kelly |
| 6,783,498 | B2 | 8/2004 | Sackner |
| 6,810,277 | B2 | 10/2004 | Edgar, Jr. et al. |
| 6,816,741 | B2 | 11/2004 | Diab |
| 6,822,564 | B2 | 11/2004 | Al-Ali |
| 6,826,419 | B2 | 11/2004 | Diab |
| 6,827,688 | B2 | 12/2004 | Goto et al. |
| 6,852,083 | B2 | 2/2005 | Caro |
| 6,855,112 | B2 | 2/2005 | Kao |
| 6,863,652 | B2 | 3/2005 | Huang et al. |
| 6,869,403 | B2 | 3/2005 | Narimatsu et al. |
| 6,929,610 | B2 | 8/2005 | Forstner |
| 6,931,269 | B2 | 8/2005 | Terry |
| 6,996,427 | B2 | 2/2006 | Ali et al. |
| 7,001,337 | B2 | 2/2006 | Dekker |
| 7,004,907 | B2 | 2/2006 | Banet |
| 7,020,507 | B2 | 3/2006 | Scharf et al. |
| 7,035,679 | B2 | 4/2006 | Addison |
| 7,043,293 | B1 | 5/2006 | Baura |
| 7,044,918 | B2 | 5/2006 | Diab |
| 7,054,453 | B2 | 5/2006 | Causevic et al. |
| 7,054,454 | B2 | 5/2006 | Causevic et al. |
| 7,070,566 | B2 | 7/2006 | Medero et al. |
| 7,074,192 | B2 | 7/2006 | Friedman et al. |
| 7,079,035 | B2 | 7/2006 | Bock et al. |
| 7,079,888 | B2 | 7/2006 | Oung |
| 7,087,025 | B2 | 8/2006 | Baruch |
| 7,171,269 | B1 | 1/2007 | Addison |
| 7,173,525 | B2 | 2/2007 | Albert |
| 7,184,809 | B1 | 2/2007 | Sterling |
| 7,203,267 | B2 | 4/2007 | De Man et al. |
| 7,215,984 | B2 | 5/2007 | Diab et al. |
| 7,215,986 | B2 | 5/2007 | Diab et al. |
| 7,225,013 | B2 | 5/2007 | Geva et al. |
| 7,252,636 | B2 | 8/2007 | Brown |
| 7,254,433 | B2 | 8/2007 | Diab et al. |
| 7,254,500 | B2 | 8/2007 | Makeig |
| 7,289,835 | B2 | 10/2007 | Mansfield |
| 7,320,030 | B2 | 1/2008 | Brown |
| 7,328,053 | B1 | 2/2008 | Diab et al. |
| 7,335,162 | B2 | 2/2008 | Eide |
| 7,376,238 | B1 | 5/2008 | Rivas et al. |
| 7,376,453 | B1 | 5/2008 | Diab et al. |
| 7,383,070 | B2 | 6/2008 | Diab et al. |
| 7,390,300 | B2 | 6/2008 | Inukai |
| 7,390,301 | B2 | 6/2008 | Skrabal |
| 7,393,327 | B2 | 7/2008 | Inukai |
| 7,400,257 | B2 | 7/2008 | Rivas |
| 7,454,240 | B2 | 11/2008 | Diab et al. |
| 7,455,643 | B1 | 11/2008 | Li et al. |
| 7,481,772 | B2 | 1/2009 | Banet |
| 7,485,095 | B2 | 2/2009 | Shusterman |
| 7,509,154 | B2 | 3/2009 | Diab et al. |
| 7,515,949 | B2 | 4/2009 | Norris |
| 7,519,488 | B2 | 4/2009 | Fu |
| 7,523,011 | B2 | 4/2009 | Akiyama et al. |
| 2002/0058876 | A1 | 5/2002 | Chen et al. |
| 2003/0163057 | A1 | 8/2003 | Flick et al. |

| | | | |
|---|---|---|---|
| 2005/0043616 | A1 | 2/2005 | Chinchoy |
| 2005/0070774 | A1 | 3/2005 | Addison et al. |
| 2005/0148885 | A1 | 7/2005 | Tweed et al. |
| 2005/0209517 | A1 | 9/2005 | Diab et al. |
| 2005/0251344 | A1 | 11/2005 | Appel et al. |
| 2005/0261594 | A1 | 11/2005 | Banet |
| 2006/0009700 | A1 | 1/2006 | Brumfield et al. |
| 2006/0063992 | A1 | 3/2006 | Yu et al. |
| 2006/0063993 | A1 | 3/2006 | Yu et al. |
| 2006/0079945 | A1 | 4/2006 | Libbus |
| 2006/0206021 | A1 | 9/2006 | Diab |
| 2006/0209631 | A1 | 9/2006 | Melese et al. |
| 2006/0217614 | A1 | 9/2006 | Takala et al. |
| 2006/0217628 | A1 | 9/2006 | Huiku |
| 2006/0229519 | A1 | 10/2006 | Fujiwara et al. |
| 2006/0241975 | A1 | 10/2006 | Brown |
| 2006/0258921 | A1 | 11/2006 | Addison et al. |
| 2006/0265022 | A1 | 11/2006 | John et al. |
| 2006/0285736 | A1 | 12/2006 | Brown |
| 2006/0287603 | A1 | 12/2006 | Bartnik et al. |
| 2007/0021673 | A1 | 1/2007 | Arbel et al. |
| 2007/0066910 | A1 | 3/2007 | Inukai et al. |
| 2007/0073120 | A1 | 3/2007 | Li et al. |
| 2007/0073124 | A1 | 3/2007 | Li et al. |
| 2007/0083093 | A1 | 4/2007 | Diab |
| 2007/0118045 | A1 | 5/2007 | Naghavi et al. |
| 2007/0167694 | A1 | 7/2007 | Causevic et al. |
| 2007/0167851 | A1 | 7/2007 | Vitali et al. |
| 2007/0225581 | A1 | 9/2007 | Diab et al. |
| 2007/0225582 | A1 | 9/2007 | Diab et al. |
| 2007/0249467 | A1 | 10/2007 | Hong et al. |
| 2007/0249918 | A1 | 10/2007 | Diab et al. |
| 2007/0282212 | A1 | 12/2007 | Sierra et al. |
| 2007/0291832 | A1 | 12/2007 | Diab et al. |
| 2008/0004514 | A1 | 1/2008 | Diab et al. |
| 2008/0015451 | A1 | 1/2008 | Hatib et al. |
| 2008/0030468 | A1 | 2/2008 | Ali et al. |
| 2008/0033305 | A1 | 2/2008 | Hatib et al. |
| 2008/0045832 | A1 | 2/2008 | McGrath |
| 2008/0082018 | A1 | 4/2008 | Sackner et al. |
| 2008/0132798 | A1 | 6/2008 | Hong et al. |
| 2008/0214903 | A1 | 9/2008 | Orbach |
| 2008/0214942 | A1 | 9/2008 | Oh et al. |
| 2008/0242955 | A1 | 10/2008 | Uutela et al. |
| 2008/0243021 | A1 | 10/2008 | Causevic et al. |
| 2009/0048497 | A1 | 2/2009 | Keren |

FOREIGN PATENT DOCUMENTS

| | | |
|---|---|---|
| GB | 2 356 251 | 5/2001 |
| GB | 2 356 252 | 5/2001 |
| JP | 03-231630 | 10/1991 |
| JP | 06-142082 | 5/1994 |
| JP | 07-136136 | 5/1995 |
| JP | 0755221 | 1/1997 |
| JP | 09-084776 | 3/1997 |
| JP | 03-225268 | 12/2003 |
| WO | WO 01/25802 | 4/2001 |
| WO | WO 01/62152 | 8/2001 |
| WO | WO 03/055395 | 7/2003 |
| WO | WO 2004/105601 | 12/2004 |
| WO | WO 2005/096170 | 10/2005 |
| WO | WO 2006/085120 | 8/2006 |
| WO | WO 2007/131064 | 11/2007 |

OTHER PUBLICATIONS

Bank, Alan J., Kaiser, Daniel R., "Smooth Muscle Relaxation: Effects on Arterial Compliance, Distensibility, Elastic modulus, and Pulse Wave Velocity," Hypertension, vol. 32, No. 2, Aug. 1998, pp. 356-359.

Berne, Robert M., Levy, Matthew N., eds., Physiology, 2nd edition, St. Louis, Mosby, 1988, pp. 357-681.

Clifton, David, Douglas, J. Graham, Addison, Paul S., Watson, James N., "Measurement of Respiratory Rate from the Photoplethysmogram in Chest Clinic Patients," Journal of Clinical Monitoring and Computing, 2006.

Finkelstein, Stanley M., Cohn, Jay N., "First- and Third-Order Models for Determining Arterial Compliance," Journal of Hypertension, vol. 10, supplement 6, Aug. 1992, pp. 511-514.

Fitchett, D., Bouthier, JD, Simon, A. Ch., Levenson, JA, Safar, ME, "Forearm Arterial Compliance: The Validation of a Plethysmographic Technique for the Measurement of Arterial Compliance," Clinical Science, vol. 67, No. 1, Jul. 1984, pp. 69-72.

Fletcher, Gerald F., ed., Cardiovascular Response to Exercise, Mt. Kisco, NY, Futura Publishing Co., 1994.

Fung, YC, Biomechanics: Circulation, 2nd Edition, New York, Springer, 1997.

Geddes, LA, Handbook of Blood Pressure Measurement, Clifton, New Jersey, Humana Press, 1991.

Legarreta, I. Romero, Addison, P. S., Reed, M. J., Grubb, N. Clegg, G. R., Robertson, C. E., Watson, J. N., "Continuous Wavelet Transform Modulus Maxima Analysis of the Electrocardiogram: Beat Characterisation and Beat-to-Beat Measurement," International Journal of Wavelets, Multiresolution and Information Processing, vol. 3, No. 1, 2004, pp. 1-24.

Leonard, Paul A., Clifton, David, Addison, Paul S., Watson, James N., Beattie, Tom "An Automated Algorithm for Determining Respiratory Rate by Photoplethysmogram In Children," Acta Paediatricia, 2006; 95: 1124-1128.

Leonard, Paul A., Douglas, J. Graham, Grubb, Neil R., Clifton, David, Addison, Paul S., Watson, James N., "A Fully Automated Algorithm for the Determination of Respiratory Rate From the Photoplethysmogram," Journal of Clinical Monitoring and Computing, 2006.

Millasseau, Sandrine C, Guigui, Franck G, Kelly, Ronan P., Prasad, Krishna, Cockcroft, John R., Ritter, James M., Chowienczyk, Philip J., Noninvasive Assessment of the Digital Volume Pulse: Comparison with the Peripheral Pressure Pulse, Hypertension, vol. 36, No. 6, Dec. 2000, pp. 952-956.

Moyle, John TB, Hahn, Cew, Adams, Anthony P, Pulse Oximetry, Revised Edition, London, BMJ, 1998.

Nara, Andrew R., Burns, Michael P., Downs, W. Gregory, Blood Pressure, Redmond, Washington, SpaceLabs, 1989.

Nichols, Wilmer W., O'Rourke, Michael F., McDonald's Blood Flow in Arteries: Theoretic, Experimental, and Clinical Principles, 3rd Edition, Philadelphia, Lea & Febiger, 1990.

O'Rourke, Michael F., Gallagher, David E., "Pulse Wave Analysis," Journal of Hypertension, vol. 14, supplement 5, Dec. 1996, pp. S147-S157.

Takazawa, Kenji, Tanaka, Nobuhiro, Fujita, Masami, Matsuoka, Osamu, Saiki, Tokuyu, Aikawa, Masaru, Tamura, Sinobu, Ibukiyama, Chiharu, "Assessment of Vasoactive Agents and Vascular Aging by the Second Derivative of Photoplethysmogram Waveform," Hypertension, vol. 32, No. 2, Aug. 1998, pp. 365-370.

Tardy, Y, Meister, JJ, Perret F, Brunner, HR, Arditi, M, "Non-Invasive Estimate of the Mechanical Properties of Peripheral Arteries from Ultrasonic and Photoplethysmographic Measurements," Clinical Physics and Physiological Measurement, vol. 12, No. 1, pp. 39-54, Feb. 1991.

Yamada, Michio, "Wavelet Analysis and Its Application," Journal of the Institute of Electronics, Information and Communication Engineers, vol. 76, No. 5, May 1993, pp. 518-528.

Young, Christopher C., Mark, Jonathan B., White, William, DeBree, Ashley, Vender, Jeffery S., Fleming, Andrew, "Clinical Evaluation of Continuous Noninvasive Blood Pressure Monitoring: Accuracy and Tracking Capabilities," Journal of Clinical Monitoring, vol. 11, No. 4, Jul. 1995, pp. 245-252.

Maja Bracic et al: "Wavelet-based Analysis of Human Blood-flow Dynamics," Bulletin of Mathematical Biology, vol. 60, No. 5, Sep. 1, 1998.

International Search Report PCT/IB2009/006217, 4 pages, mailed Oct. 14, 2009.

US 8,506,498 B2

SYSTEMS AND METHODS USING INDUCED PERTURBATION TO DETERMINE PHYSIOLOGICAL PARAMETERS

CROSS-REFERENCE TO RELATED APPLICATIONS

This claims the benefit of U.S. Provisional Patent Application No. 61/080,953, filed Jul. 15, 2008, which is hereby incorporated by reference herein in its entirety.

SUMMARY

The present disclosure relates to blood pressure monitoring and, more particularly, the present disclosure relates to systems and methods for non-invasive blood pressure monitoring using induced perturbations.

In one embodiment, an exciter may induce a perturbation in a patient. A probe or sensor may then detect a signal, such as a photoplethysmograph (PPG) signal, a pressure signal, a blood flow signal, or a blood volume signal, for example, for use with a continuous non-invasive blood pressure (referred to herein as "CNIBP") monitoring system or pulse oximeter. The probe or sensor could be, for example, an optical sensor, a piezo-electric sensor, a pressure sensor, and ultrasound sensor, or a Doppler sensor, among others. The signal obtained from the sensor or probe may then be used to measure or determine one or more physiological parameters of the patient. For example, if the perturbations are based on a known signal, any differences between the known signal and the input signal may be attributable to the patient's physiological parameters.

The time required for a physiological pulse to travel a certain distance may be related to a patient's blood pressure. Chen et al. U.S. Pat. No. 6,599,251, which is hereby incorporated by reference herein in its entirety, discloses some techniques for continuous and non-invasive blood pressure monitoring using the relationship between pulse propagation time and blood pressure that may be used in conjunction with the present disclosure. Given this relationship, any changes in the input signal's phase relative to the phase of the known signal, on which the perturbations are based, may be attributable to changes in the patient's blood pressure. In an embodiment, the input signal may be analyzed to determine its phase composition relative to the known signal and any changes in phase may be indicative of one or more physiological parameters of the patient (e.g., the patient's blood pressure). Therefore, the patient's blood pressure may be measured continuously or periodically using the phase composition of the detected signal.

In one embodiment, past blood pressure measurements may be used to refine current and future blood pressure measurements. For example, in one suitable approach, detected blood pressure values outside some pre-defined threshold calculated according to, for example, a moving average, may be ignored. Additionally or alternatively, detected blood pressure values outside of a pre-defined threshold calculated according to, for example, a moving average, may automatically signal a recalibration event.

A recalibration event may automatically trigger a recalibration sequence. A recalibration sequence may be performed at any suitable time. For example, a recalibration sequence may be performed: 1) initially after device or monitoring initialization; 2) after signaled recalibration events; 3) periodically on a predetermined or other suitable event-driven schedule; 4) at the request of the device user; or 5) at any combination of the aforementioned times. In addition, in one embodiment, the control signal used to induce perturbations may be varied during (or immediately after) any recalibration sequence. As such, a flexible and adaptive approach may be used in order to improve blood pressure measurements derived from a PPG (or pressure, blood volume, blood flow, etc.) signal on-the-fly.

Recalibration may be performed, in one embodiment, by measuring a patient's blood pressure (or a reference blood pressure) and then measuring the phase composition of the patient's PPG (or other) signal. Updated or refined values for one or more constants or parameters used in the blood pressure measurement determination may then be computed based at least in part on the recalibration. These updated or refined constant or parameter values may then be used to determine the patient's blood pressure until the next recalibration sequence is performed (or for some predetermined length of time).

In an embodiment, the phase of the continuous wavelet transform (CWT) of a detected signal may be compared between an exciter location and a sensor or probe location. The scalogram of the detected signal at the exciter location and the scalogram of the detected signal at the sensor or probe location may then be compared at different scales to determine phase drift. In an embodiment, the selected scales analyzed may be those scales of characteristic frequency close to the frequency of the exciter. The determined phase drift may then be used to identify dispersion and attenuation of the induced perturbation signal. The measured phase drift may also be used as a proxy for pulse wave velocity and estimated blood pressure measurements may be determined.

BRIEF DESCRIPTION OF THE DRAWINGS

The above and other features of the present disclosure, its nature and various advantages will be more apparent upon consideration of the following detailed description, taken in conjunction with the accompanying drawings in which.

DETAILED DESCRIPTION

Figure 1:
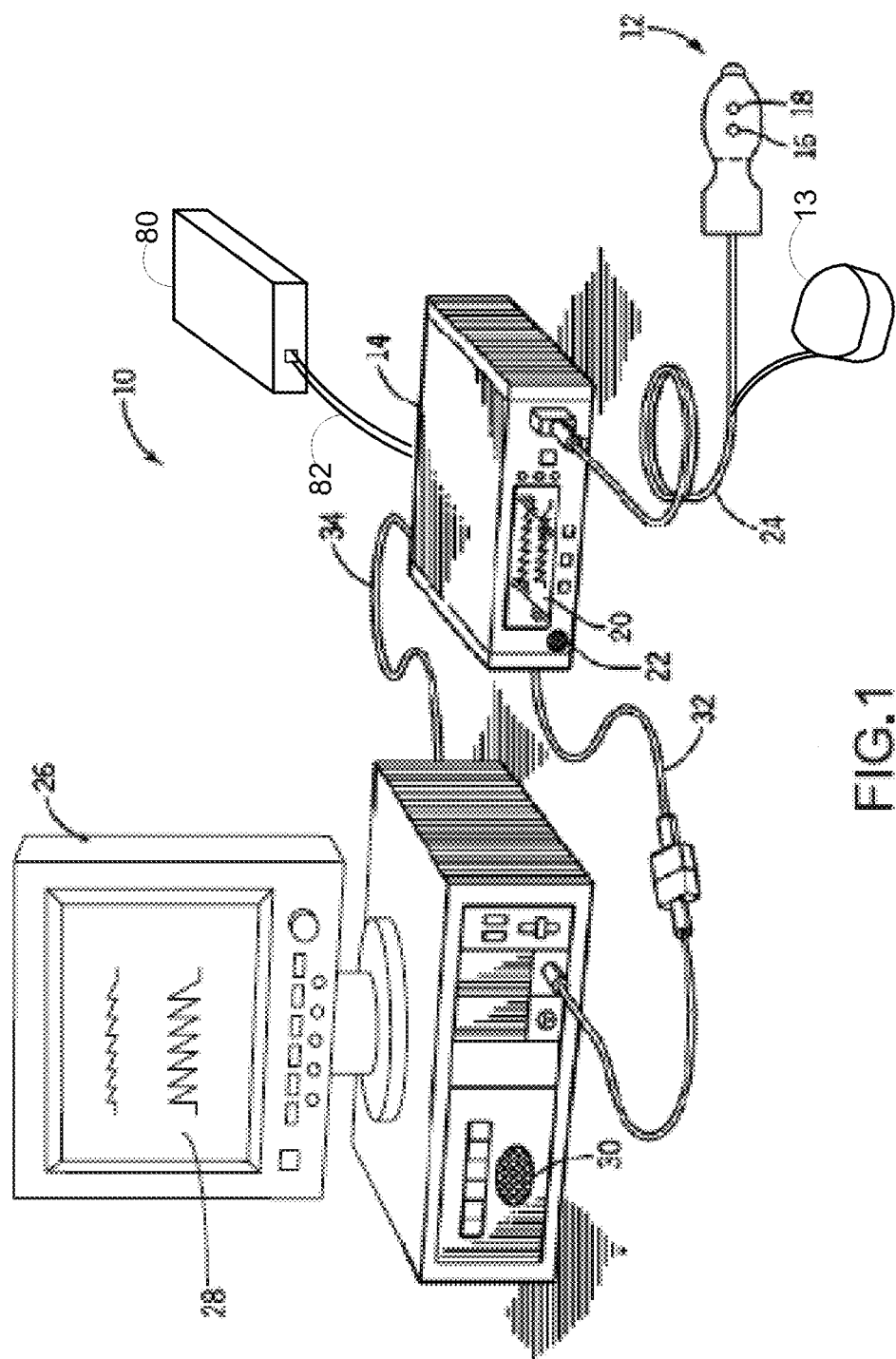
FIG. 1 shows an illustrative CNIBP monitoring system in accordance with an embodiment.

Some CNIBP monitoring techniques utilize two probes or sensors positioned at two different locations on a subject's body. The elapsed time (i.e., time difference), T, between the arrival of corresponding points of respective signals indicative of physiological pulses, such as, for example, photoplethysmograph (PPG) signals, at the two locations may then be determined using signals obtained by the two probes or sensors. The estimated blood pressure, p, may then be related to the elapsed time, T, by $$p = a + b \cdot \ln(T) \qquad (1)$$

where a and b are constants that may be dependent upon the nature of the subject and the nature of the pulse detecting devices. Other suitable equations using an elapsed time between corresponding points of pulse signals may also be used to derive an estimated blood pressure measurement.

Equation (1) may be used to determine the estimated blood pressure from the time difference, T, between corresponding points of pulse signals received by two respective sensors or probes attached to two different locations of a subject. The value used for the time difference, T, in equation (1) (or in any other blood pressure equation using an elapsed time value between corresponding points of pulse signals) may also be derived from a pulse signal obtained from a single sensor or probe. In one embodiment, the pulse signal obtained from the single sensor or probe may take the form of a PPG signal obtained, for example, from a CNIBP monitoring system or pulse oximeter.

A PPG signal may be used to determine blood pressure at least in part because the shape of the PPG signal may be considered to be made up of a pulse wave and its many reflections throughout the circulatory system. As such, blood pressure equations used in continuous blood pressure monitoring techniques that use sensors or probes at two locations (e.g., equation (1) above) may also be used with continuous blood pressure monitoring techniques that use only a single probe. As described in more detail below, characteristic points may be identified in a detected PPG signal. To determine blood pressure using a PPG signal, the time difference, T, in equation (1) (or in any other blood pressure equation using the time between corresponding points of pulse signals) may then be substituted with the time between two characteristic points in a detected PPG signal.

In accordance with the disclosure, perturbations may be induced in a patient and used to measure a physiological parameter of a patient (e.g., a patient's blood pressure). An exciter (e.g., an ultrasonic, acoustic, or mechanical exciter) may be provided against or near the patient's tissue for inducing the perturbations. An input signal obtained from a sensor or probe may then be used to measure one or more physiological parameters of the patient. For example, if the perturbations are based on a known signal, any differences between the known signal and the input signal may be attributable to the patient's physiological parameters, such as blood pressure. For example, the drift in phase between the CWT of a detected signal at the exciter location and the CWT of a detected signal at a sensor or probe location may be used to determine a patient's blood pressure. Assuming a constant propagation, this phase drift may be used as a proxy for pulse wave velocity. The elapsed time, T, may then be computed and used in connection with equation (1) to determine estimated blood pressure.

Inducing a perturbation in a patient can allow for increased accuracy and reliability when determining the patient's blood pressure (or any other physiological parameter). A patient's natural pulse may, for example, be relatively insignificant with respect to other noise in the circulatory system so any effects of an induced perturbation (e.g., changes in amplitude and/or phase composition) may be more pronounced in a PPG signal. Moreover, different patients' natural pulses may each have different features making them more difficult to automatically identify in a PPG signal than an induced perturbation. Additionally, the known signal on which the induced perturbations are based may be designed so that the perturbations have easily identifiable features.

FIG. 1 is a perspective view of an embodiment of a CNIBP monitoring system 10 that may also be used to perform pulse oximetry. System 10 may include a sensor 12, exciter 13, and a monitor 14. Sensor 12 may include an emitter 16 for emitting light at one or more wavelengths into a patient's tissue. A detector 18 may also be provided in sensor 12 for detecting the light originally from emitter 16 that emanates from the patient's tissue after passing through the tissue.

According to another embodiment and as will be described, system 10 may include a plurality of sensors forming a sensor array in lieu of single sensor 12. Each of the sensors of the sensor array may be a complementary metal oxide semiconductor (CMOS) sensor. Alternatively, each sensor of the array may be charged coupled device (CCD) sensor. In another embodiment, the sensor array may be made up of a combination of CMOS and CCD sensors. The CCD sensor may comprise a photoactive region and a transmission region for receiving and transmitting data whereas the CMOS sensor may be made up of an integrated circuit having an array of pixel sensors. Each pixel may have a photodetector and an active amplifier.

According to an embodiment, emitter 16 and detector 18 may be on opposite sides of a digit such as a finger or toe, in which case the light that is emanating from the tissue has passed completely through the digit. In an embodiments, emitter 16 and detector 18 may be arranged on opposite sides of an earlobe such that the light that is emanating from the tissue has passed completely through the earlobe. In an embodiment, emitter 16 and detector 18 may be arranged so that light from emitter 16 penetrates the tissue and is reflected by the tissue into detector 18, such as a sensor designed to obtain pulse oximetry or CNIBP data from a patient's forehead.

System 10 may include exciter 13 for inducing perturbations in a patient. Exciter 13 may include any device suitable for inducing a mechanical perturbation in a patient. Exciter 13 may vibrate or otherwise apply pressure to a patient's body to induce perturbations. For example, exciter 13 may include an occluding cuff suitable for deployment on a patient's appendage (e.g., an arm or a leg). The cuff may then compress a patient's tissue to induce perturbations in the patient. In one embodiment, a cuff may include a mechanical actuator for inducing relatively subtle perturbations in the patient. In another example, exciter 13 may include an acoustic element for providing high-frequency perturbations. In yet another example, exciter 13 may be provided in a probe or other device that can be placed adjacent to or within a patient. Exciter 13 may be provided within a certain distance of sensor 12 so that the effect of perturbations induced by exciter 13 can be easily measured by sensor 12. Therefore if sensor 12 is provided on a patient's digit, exciter 13 may be deployed on the patient's appendage related to that digit. For example, sensor 12 may be deployed on a finger on the patient's right hand, and exciter 13 may be deployed on the patient's right arm.

Monitor 14 may control the operation of exciter 13. Monitor 14 may be able to precisely control the time at which exciter 13 induces perturbations. In one embodiment, monitor 14 may be able to control the type of perturbations induced by exciter 13. Monitor 14 may, for example, provide one or more precise control signals to exciter 13. The control signal may specify the time for inducing a perturbation or the type of perturbation to be induced. In one embodiment, exciter 13 may provide a notification signal to monitor 14 to notify monitor 14 when a perturbation is induced.

In an embodiment, exciter 13, sensor 12, or the sensor array may be connected to and draw its power from monitor 14 as shown. In another embodiment, the exciter or the sensor may be wirelessly connected to monitor 14 and include its own battery or similar power supply (not shown). Monitor 14 may be configured to calculate physiological parameters (e.g., blood pressure) based at least in part on a control signal provided to exciter 13 and data received from sensor 12 relating to light emission and detection. Further, monitor 14 may include a display 20 configured to display physiological parameters or other information about the system. In the embodiment shown, monitor 14 may also include a speaker 22 to provide an audible sound. For example, speaker 22 may provide an audible alarm in the event that a patient's physiological parameters are not within a predefined normal range.

In one embodiment, exciter 13, sensor 12, or the sensor array, may be communicatively coupled to monitor 14 via a cable 24. However, in other embodiments, a wireless transmission device (not shown) or the like may be used instead of or in addition to cable 24.

In the illustrated embodiment, system 10 may also include a multi-parameter patient monitor 26. The monitor may be cathode ray tube type, a flat panel display (as shown) such as a liquid crystal display (LCD) or a plasma display, or any other type of monitor now known or later developed. Multi-parameter patient monitor 26 may be configured to calculate physiological parameters and to provide a display 28 for information from monitor 14 and from other medical monitoring devices or systems (not shown). For example, multi-parameter patient monitor 26 may be configured to display an estimate of a patient's blood pressure from monitor 14, blood oxygen saturation generated by monitor 14 (referred to as an "SpO$_2$" measurement), and pulse rate information from monitor 14.

Monitor 14 may be communicatively coupled to multi-parameter patient monitor 26 via a cable 32 or 34 that is coupled to a sensor input port or a digital communications port, respectively and/or may communicate wirelessly (not shown). In addition, monitor 14 and/or multi-parameter patient monitor 26 may be coupled to a network to enable the sharing of information with servers or other workstations (not shown). Monitor 14 may be powered by a battery (not shown) or by a conventional power source such as a wall outlet.

Calibration device 80, which may be powered by monitor 14, a battery, or by a conventional power source such as a wall outlet, may include any suitable blood pressure calibration device. For example, calibration device 80 may take the form of any invasive or non-invasive blood pressure monitoring or measuring system used to generate reference blood pressure measurements for use in calibrating the CNIBP monitoring techniques described herein. Such calibration devices may include, for example, an aneroid or mercury sphygmomanometer and occluding cuff, a pressure sensor inserted directly into a suitable artery of a patient, or any other device or mechanism used to sense, measure, determine, or derive a reference blood pressure measurement. In one embodiment, calibration device 80 may utilize one or more portions of exciter 13 (e.g., an ultrasonic, acoustic, or mechanical exciter) to determine a reference blood pressure measurement. For example, if exciter 13 includes an occluding cuff, calibration device 80 may use the cuff to determine a reference blood pressure measurement. In one embodiment, calibration device 80 may include a manual input device (not shown) used by an operator to manually input reference blood pressure measurements obtained from some other source (e.g., an external invasive or non-invasive blood pressure measurement system).

Calibration device 80 may also access reference blood pressure measurements stored in memory (e.g., RAM, ROM, or a storage device). For example, in one embodiment calibration device 80 may access reference blood pressure measurements from a relational database stored within calibration device 80, monitor 14, or multi-parameter patient monitor 26. As described in more detail below, the reference blood pressure measurements generated or accessed by calibration device 80 may be updated in real-time, resulting in a continuous source of reference blood pressure measurements for use in continuous or periodic calibration. Alternatively, reference blood pressure measurements generated or accessed by calibration device 80 may be updated periodically, and calibration may be performed on the same periodic cycle. In the depicted embodiment, calibration device 80 is connected to monitor 14 via cable 82. In another embodiment, calibration device 80 may be a stand-alone device that may be in wireless communication with monitor 14. Reference blood pressure measurements may then be wirelessly transmitted to monitor 14 for use in calibration. In still another embodiment, calibration device 80 is completely integrated within monitor 14.

Figure 2:
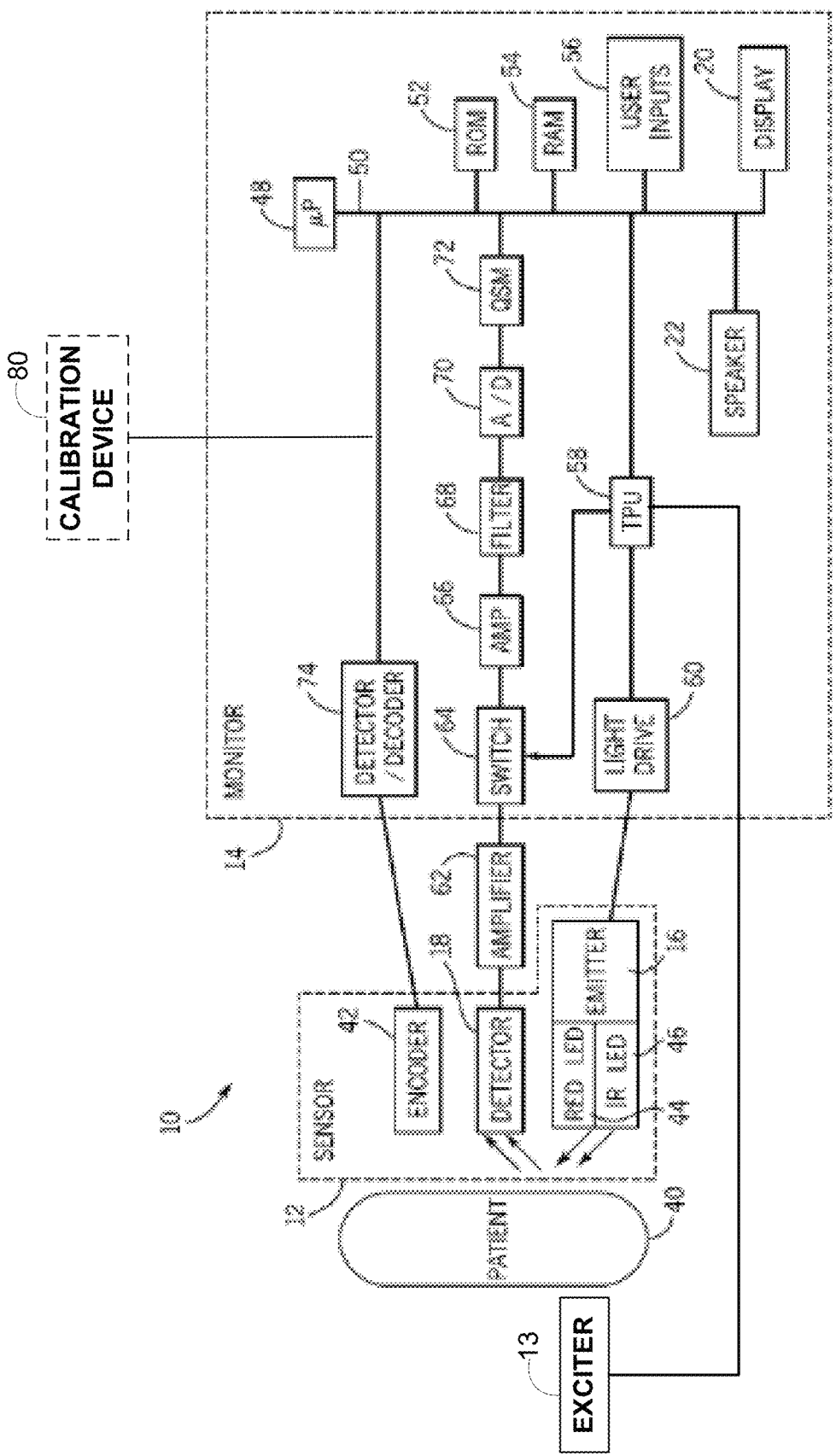
FIG. 2 is a block diagram of the illustrative CNIBP monitoring system of FIG. 1 coupled to a patient in accordance with an embodiment.

FIG. 2 is a block diagram of a CNIBP monitoring system, such as system 10 of FIG. 1, which may be coupled to a patient 40 in accordance with an embodiment. System 10 may include exciter 13 for inducing one or more perturbations in patient 40. Exciter 13 may be provided in contact with the tissue of patient 40. Exciter 13 may include one or more moving parts adjacent to the tissue of patient 40. Accordingly, exciter 13 may induce perturbations in patient 40 when the one or more moving parts are activated. Monitor 14 may be connected with exciter 13 for providing electric power to the exciter or controlling the exciter. For example, monitor 14 may provide electric power and a control signal to exciter 13.

Certain illustrative components of sensor 12 and monitor 14 are illustrated in FIG. 2. Sensor 12 may include emitter 16, detector 18, and encoder 42. In the embodiment shown, emitter 16 may be configured to emit at least one wavelength of light (e.g., RED or IR) into a patient's tissue 40. For calculating SpO$_2$, emitter 16 may include a RED light emitting light source such as RED light emitting diode (LED) 44 and an IR light emitting light source such as IR LED 46 for emitting light into the patient's tissue 40. In other embodiments, emitter 16 may include a light emitting light source of a wavelength other than RED or IR. In one embodiment, the RED wavelength may be between about 600 nm and about 700 nm, and the IR wavelength may be between about 800 nm and about 1000 nm. In embodiments where a sensor array is used in place of single sensor, each sensor may be configured to emit a single wavelength. For example, a first sensor emits only a RED light while a second only emits an IR light.

It will be understood that, as used herein, the term "light" may refer to energy produced by radiative sources and may include one or more of ultrasound, radio, microwave, millimeter wave, infrared, visible, ultraviolet, gamma ray or X-ray electromagnetic radiation. As used herein, light may also include any wavelength within the radio, microwave, infrared, visible, ultraviolet, or X-ray spectra, and that any suitable wavelength of electromagnetic radiation may be appropriate for use with the present techniques. Detector 18 may be chosen to be specifically sensitive to the chosen targeted energy spectrum of the emitter 16.

In an embodiment, detector 18 may be configured to detect the intensity of light at the emitted wavelengths (or any other suitable wavelength). Alternatively, each sensor in a sensor array may be configured to detect an intensity of a single wavelength. In operation, light may enter detector 18 after passing through the patient's tissue 40. Detector 18 may convert the intensity of the received light into an electrical signal. The light intensity is directly related to the absorbance and/or reflectance of light in the tissue 40. That is, when more light at a certain wavelength is absorbed or reflected, less light of that wavelength is received from the tissue by the detector 18. After converting the received light to an electrical signal, detector 18 may send the signal to monitor 14, where physiological parameters may be calculated based at least partially on the absorption of one or more of the RED and IR (or other suitable) wavelengths in the patient's tissue 40.

In an embodiment, encoder 42 may contain information about sensor 12, such as what type of sensor it is (e.g., whether the sensor is intended for placement on a forehead or digit) and the wavelength or wavelengths of light emitted by emitter 16. This information may be used by monitor 14 to select appropriate algorithms, lookup tables and/or calibration coefficients stored in monitor 14 for calculating the patient's physiological parameters.

Encoder 42 may contain information specific to patient 40, such as, for example, the patient's age, weight, and diagnosis. This information may allow monitor 14 to determine, for example, patient-specific threshold ranges in which the patient's physiological parameter measurements should fall and to enable or disable additional physiological parameter algorithms. Encoder 42 may, for instance, be a coded resistor which stores values corresponding to the type of sensor 12 or the type of each sensor in the sensor array, the wavelength or wavelengths of light emitted by emitter 16 on each sensor of the sensor array, and/or the patient's characteristics. In another embodiment, encoder 42 may include a memory on which one or more of the following information may be stored for communication to monitor 14: the type of the sensor 12; the wavelength or wavelengths of light emitted by emitter 16; the particular wavelength each sensor in the sensor array is monitoring; a signal threshold for each sensor in the sensor array; any other suitable information; or any combination thereof.

In an embodiment, signals from detector 18 and encoder 42 may be transmitted to monitor 14. In the embodiment shown, monitor 14 may include a general-purpose microprocessor 48 connected to an internal bus 50. Microprocessor 48 may be adapted to execute software, which may include an operating system and one or more applications, as part of performing the functions described herein. Also connected to bus 50 may be a read-only memory (ROM) 52, a random access memory (RAM) 54, user inputs 56, display 20, and speaker 22.

RAM 54 and ROM 52 are illustrated by way of example, and not limitation. Any suitable computer-readable media may be used in the system for data storage. Computer-readable media are capable of storing information that can be interpreted by microprocessor 48. This information may be data or may take the form of computer-executable instructions, such as software applications, that cause the microprocessor to perform certain functions and/or computer-implemented methods. Depending on the embodiment, such computer-readable media may include computer storage media and communication media. Computer storage media may include volatile and non-volatile, removable and non-removable media implemented in any method or technology for storage of information such as computer-readable instructions, data structures, program modules or other data. Computer storage media may include, but is not limited to, RAM, ROM, EPROM, EEPROM, flash memory or other solid state memory technology, CD-ROM, DVD, or other optical storage, magnetic cassettes, magnetic tape, magnetic disk storage or other magnetic storage devices, or any other medium which can be used to store the desired information and which can be accessed by components of the system.

In the embodiment shown, a time processing unit (TPU) 58 may control the operation of sensor 12 and exciter 13. TPU 58 may include precise timing circuitry for controlling the operation of sensor 12 and exciter 13. For example, TPU 58 may precisely control the timing of perturbations induced by exciter 13. TPU 58 may provide timing control signals to a light drive circuitry 60, which may control when emitter 16 is illuminated and multiplexed timing for the RED LED 44 and the IR LED 46. TPU 58 may also control the gating-in of signals from detector 18 through an amplifier 62 and a switching circuit 64. These signals are sampled at the proper time, depending upon which light source is illuminated. The received signal from detector 18 may be passed through an amplifier 66, a low pass filter 68, and an analog-to-digital converter 70. The digital data may then be stored in a queued serial module (QSM) 72 (or buffer) for later downloading to RAM 54 as QSM 72 fills up. In one embodiment, there may be multiple separate parallel paths having amplifier 66, filter 68, and A/D converter 70 for multiple light wavelengths or spectra received.

In an embodiment, microprocessor 48 may determine the patient's physiological parameters, such as blood pressure, $SpO_2$, and pulse rate, using various techniques and/or look-up tables based at least partially on the value of the received signals and/or data corresponding to the light received by detector 18. Signals corresponding to information about patient 40, and particularly about the intensity of light emanating from a patient's tissue over time, may be transmitted from encoder 42 to a decoder 74. These signals may include, for example, encoded information relating to patient characteristics. Decoder 74 may translate these signals to enable the microprocessor to determine the thresholds based on algorithms or look-up tables stored in ROM 52. User inputs 56 may be used to enter information about the patient, such as age, weight, height, diagnosis, medications, treatments, and so forth. In an embodiment, display 20 may exhibit a list of values which may generally apply to the patient, such as, for example, age ranges or medication families, which the user may select using user inputs 56.

The optical signal through the tissue can be degraded by noise, among other sources. One source of noise is ambient light that reaches the light detector. Another source of noise is electromagnetic coupling from other electronic instruments. Movement of the patient also introduces noise and affects the signal. For example, the contact between the detector and the skin, or the emitter and the skin, can be temporarily disrupted when movement causes either to move away from the skin. In addition, because blood is a fluid, it responds differently than the surrounding tissue to inertial effects, thus resulting in momentary changes in volume at the point to which the sensor or probe is attached.

Noise (e.g., from patient movement) can degrade a CNIBP or pulse oximetry signal relied upon by a physician, without the physician's awareness. This is especially true if the monitoring of the patient is remote, the motion is too small to be observed, or the doctor is watching the instrument or other parts of the patient, and not the sensor site. Processing CNIBP or pulse oximetry (i.e., PPG) signals may involve operations that reduce the amount of noise present in the signals or otherwise identify noise components in order to prevent them from affecting measurements of physiological parameters derived from the PPG signals.

CNIBP monitoring system 10 may also include calibration device 80. Although shown external to monitor 14 in the example of FIG. 2, calibration device 80 may additionally or alternatively be internal to monitor 14. Calibration device 80 may be coupled to internal bus 50 of monitor 14. As described in more detail below, reference blood pressure measurements from calibration device 80 may be accessed by microprocessor 48 for use in calibrating the CNIBP measurements.

It will be understood that the present disclosure is applicable to any suitable signals and that PPG signals are used merely for illustrative purposes. Those skilled in the art will recognize that the present disclosure has wide applicability to other signals including, but not limited to other biosignals (e.g., electrocardiogram, electroencephalogram, electrogastrogram, electromyogram, heart rate signals, pathological sounds, ultrasound, pressure signals, blood volume signal, blood flow signals, or any other suitable biosignal) and/or any other suitable signals, and/or any combination thereof.

In one embodiment, a PPG signal may be transformed using a continuous wavelet transform. Information derived from the transform of the PPG signal (i.e., in wavelet space) may be used to provide measurements of one or more physiological parameters. For example, the continuous wavelet transform of the PPG signal can be analyzed to determine the phase composition of the input signal, and the phase composition can be used to determine the patient's blood pressure.

The continuous wavelet transform of a signal x(t) in accordance with the present disclosure may be defined as $$T(a,b) = \frac{1}{\sqrt{a}} \int_{-\infty}^{+\infty} x(t) \psi^* \left( \frac{t-b}{a} \right) dt \qquad (2)$$

where $\psi^*(t)$ is the complex conjugate of the wavelet function $\psi(t)$, a is the dilation parameter of the wavelet and b is the location parameter of the wavelet. The transform given by equation (2) may be used to construct a representation of a signal on a transform surface. The transform may be regarded as a time-scale representation. Wavelets are composed of a range of frequencies, one of which may be denoted as the characteristic frequency of the wavelet, where the characteristic frequency associated with the wavelet is inversely proportional to the scale a. One example of a characteristic frequency is the dominant frequency. Each scale of a particular wavelet may have a different characteristic frequency. The underlying mathematical detail required for the implementation within a time-scale can be found, for example, in Paul S. Addison, The Illustrated Wavelet Transform Handbook (Taylor & Francis Group 2002), which is hereby incorporated by reference herein in its entirety.

The continuous wavelet transform decomposes a signal using wavelets, which are generally highly localized in time. The continuous wavelet transform may provide a higher resolution relative to discrete transforms, thus providing the ability to garner more information from signals than typical frequency transforms such as Fourier transforms (or any other spectral techniques) or discrete wavelet transforms. Continuous wavelet transforms allow for the use of a range of wavelets with scales spanning the scales of interest of a signal such that small scale signal components correlate well with the smaller scale wavelets and thus manifest at high energies at smaller scales in the transform. Likewise, large scale signal components correlate well with the larger scale wavelets and thus manifest at high energies at larger scales in the transform. Thus, components at different scales may be separated and extracted in the wavelet transform domain. Moreover, the use of a continuous range of wavelets in scale and time position allows for a higher resolution transform than is possible relative to discrete techniques.

In addition, transforms and operations that convert a signal or any other type of data into a spectral (i.e., frequency) domain necessarily create a series of frequency transform values in a two-dimensional coordinate system where the two dimensions may be frequency and, for example, amplitude. For example, any type of Fourier transform would generate such a two-dimensional spectrum. In contrast, wavelet transforms, such as continuous wavelet transforms, are required to be defined in a three-dimensional coordinate system and generate a surface with dimensions of time, scale and, for example, amplitude. Hence, operations performed in a spectral domain cannot be performed in the wavelet domain; instead the wavelet surface must be transformed into a spectrum (i.e., by performing an inverse wavelet transform to convert the wavelet surface into the time domain and then performing a spectral transform from the time domain). Conversely, operations performed in the wavelet domain cannot be performed in the spectral domain; instead a spectrum must first be transformed into a wavelet surface (i.e., by performing an inverse spectral transform to convert the spectral domain into the time domain and then performing a wavelet transform from the time domain). Nor does a cross-section of the three-dimensional wavelet surface along, for example, a particular point in time equate to a frequency spectrum upon which spectral-based techniques may be used. At least because wavelet space includes a time dimension, spectral techniques and wavelet techniques are not interchangeable. It will be understood that converting a system that relies on spectral domain processing to one that relies on wavelet space processing would require significant and fundamental modifications to the system in order to accommodate the wavelet space processing (e.g., to derive a representative energy value for a signal or part of a signal requires integrating twice, across time and scale, in the wavelet domain while, conversely, one integration across frequency is required to derive a representative energy value from a spectral domain). As a further example, to reconstruct a temporal signal requires integrating twice, across time and scale, in the wavelet domain while, conversely, one integration across frequency is required to derive a temporal signal from a spectral domain. It is well known in the art that, in addition to or as an alternative to amplitude, parameters such as energy density, modulus, phase, among others may all be generated using such transforms and that these parameters have distinctly different contexts and meanings when defined in a two-dimensional frequency coordinate system rather than a three-dimensional wavelet coordinate system. For example, the phase of a Fourier system is calculated with respect to a single origin for all frequencies while the phase for a wavelet system is unfolded into two dimensions with respect to a wavelet's location (often in time) and scale.

The energy density function of the wavelet transform, the scalogram, is defined as $$S(a,b) = |T(a,b)|^2 \qquad (3)$$

where '||' is the modulus operator. The scalogram may be rescaled for useful purposes. One common rescaling is defined as $$S_R(a,b) = \frac{|T(a,b)|^2}{a} \qquad (4)$$

and is useful for defining ridges in wavelet space when, for example, the Morlet wavelet is used. Ridges are defined as the locus of points of local maxima in the plane. Any reasonable definition of a ridge may be employed in the method. Also included as a definition of a ridge herein are paths displaced from the locus of the local maxima. A ridge associated with only the locus of points of local maxima in the plane are labeled a "maxima ridge".

For implementations requiring fast numerical computation, the wavelet transform may be expressed as an approximation using Fourier transforms. Pursuant to the convolution theorem, because the wavelet transform is the cross-correlation of the signal with the wavelet function, the wavelet transform may be approximated in terms of an inverse FFT of the product of the Fourier transform of the signal and the Fourier transform of the wavelet for each required a scale and then multiplying the result by $\sqrt{a}$.

In the discussion of the technology which follows herein, the "scalogram" may be taken to include all suitable forms of rescaling including, but not limited to, the original unsealed wavelet representation, linear rescaling, any power of the modulus of the wavelet transform, or any other suitable resealing. In addition, for purposes of clarity and conciseness, the term "scalogram" shall be taken to mean the wavelet transform, T(a,b) itself, or any part thereof. For example, the real part of the wavelet transform, the imaginary part of the wavelet transform, the phase of the wavelet transform, any other suitable part of the wavelet transform, or any combination thereof is intended to be conveyed by the term "scalogram".

A scale, which may be interpreted as a representative temporal period, may be converted to a characteristic frequency of the wavelet function. The characteristic frequency associated with a wavelet of arbitrary a scale is given by $$f = \frac{f_c}{a} \quad (5)$$

where $f_c$, the characteristic frequency of the mother wavelet (i.e., at a=1), becomes a scaling constant and f is the representative or characteristic frequency for the wavelet at arbitrary scale a.

Any suitable wavelet function may be used in connection with the present disclosure. One of the most commonly used complex wavelets, the Morlet wavelet, is defined as:

$$\psi(t) = \pi^{-1/4}(e^{i2\pi f_0 t} - e^{-(2\pi f_0)^2/2})e^{-t^2/2} \quad (6)$$

where $f_0$ is the central frequency of the mother wavelet. The second term in the parenthesis is known as the correction term, as it corrects for the non-zero mean of the complex sinusoid within the Gaussian window. In practice, it becomes negligible for values of $f_0 \gg 0$ and can be ignored, in which case, the Morlet wavelet can be written in a simpler form as $$\psi(t) = \frac{1}{\pi^{1/4}} e^{i2\pi f_0 t} e^{-t^2/2} \quad (7)$$

This wavelet is a complex wave within a scaled Gaussian envelope. While both definitions of the Morlet wavelet are included herein, the function of equation (7) is not strictly a wavelet as it has a non-zero mean (i.e., the zero frequency term of its corresponding energy spectrum is non-zero). However, it will be recognized by those skilled in the art that equation (7) may be used in practice with $f_0 \gg 0$ with minimal error and is included (as well as other similar near wavelet functions) in the definition of a wavelet herein. A more detailed overview of the underlying wavelet theory, including the definition of a wavelet function, can be found in the general literature. Discussed herein is how wavelet transform features may be extracted from the wavelet decomposition of signals. For example, wavelet decomposition of PPG signals may be used to provide clinically useful information within a medical device.

Figure 3B:
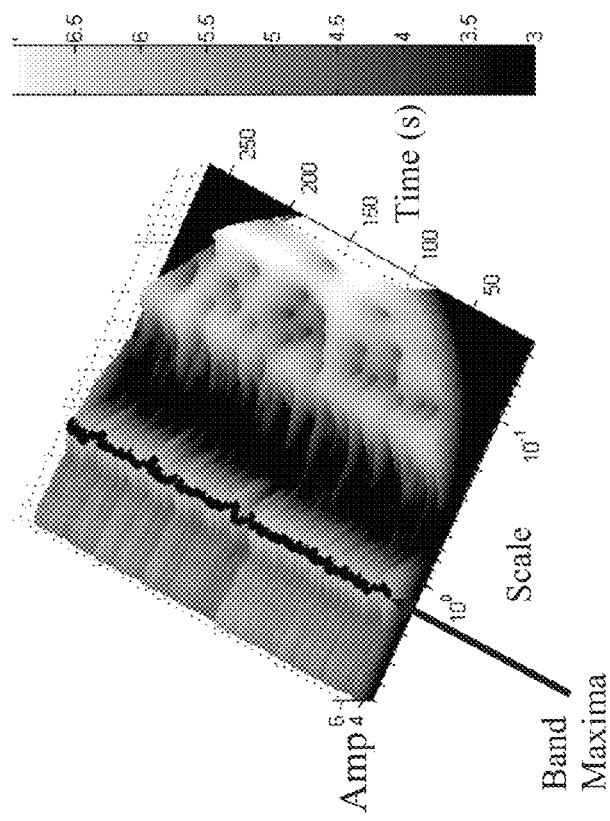
FIGS. 3(a) and 3(b) show illustrative views of a scalogram derived from a PPG signal in accordance with an embodiment.
Figure 3A:
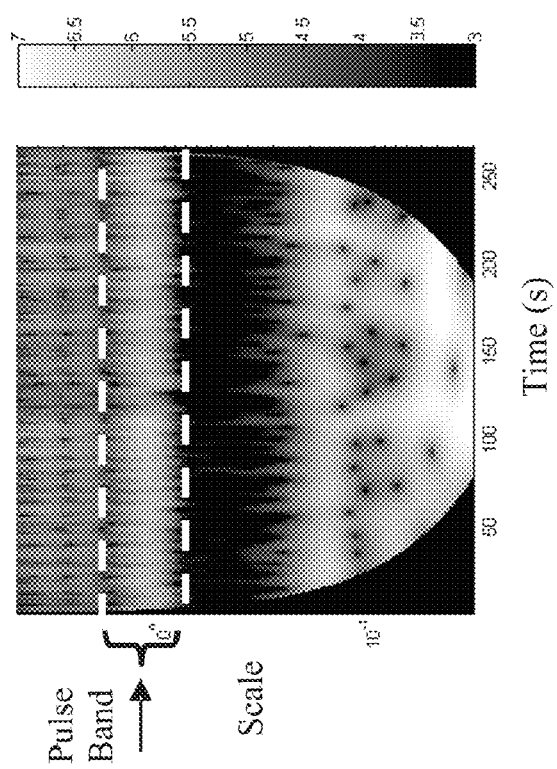

Pertinent repeating features in a signal give rise to a time-scale band in wavelet space or a rescaled wavelet space. For example, the pulse component of a PPG signal produces a dominant band in wavelet space at or around the pulse frequency. FIGS. 3(a) and (b) show two views of an illustrative scalogram derived from a PPG signal, according to an embodiment. The figures show an example of the band caused by the pulse component in such a signal. The pulse band is located between the dashed lines in the plot of FIG. 3(a). The band is formed from a series of dominant coalescing features across the scalogram. This can be clearly seen as a raised band across the transform surface in FIG. 3(b) located within the region of scales indicated by the arrow in the plot (corresponding to 60 beats per minute). The maxima of this band with respect to scale is the ridge. The locus of the ridge is shown as a black curve on top of the band in FIG. 3(b). By employing a suitable rescaling of the scalogram, such as that given in equation (4), the ridges found in wavelet space may be related to the instantaneous frequency of the signal. In this way, the pulse rate may be obtained from the PPG signal. Instead of resealing the scalogram, a suitable predefined relationship between the scale obtained from the ridge on the wavelet surface and the actual pulse rate may also be used to determine the pulse rate.

By mapping the time-scale coordinates of the pulse ridge onto the wavelet phase information gained through the wavelet transform, individual pulses may be captured. In this way, both times between individual pulses and the timing of components within each pulse may be monitored and used to detect heart beat anomalies, measure arterial system compliance, or perform any other suitable calculations or diagnostics. Alternative definitions of a ridge may be employed. Alternative relationships between the ridge and the pulse frequency of occurrence may be employed.

Figure 3C:
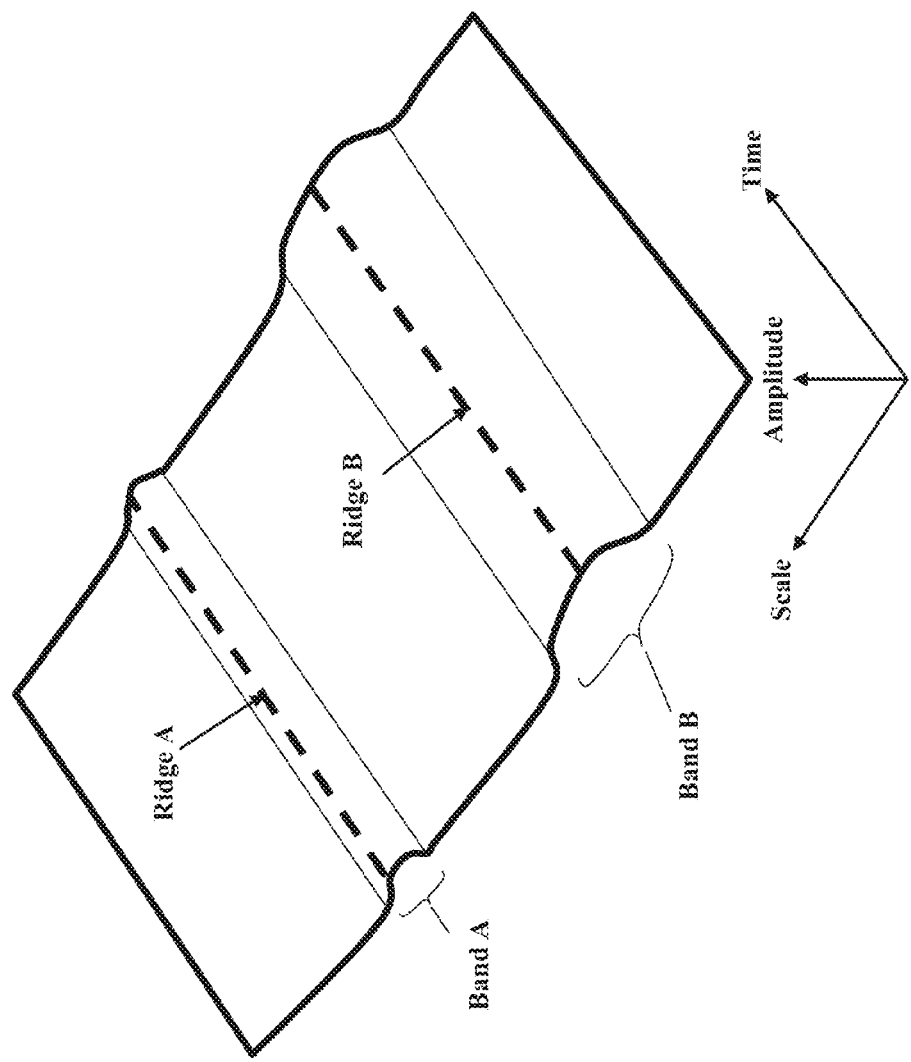
FIG. 3(c) shows an illustrative scalogram derived from a signal containing two pertinent components in accordance with an embodiment.
Figure 3D:
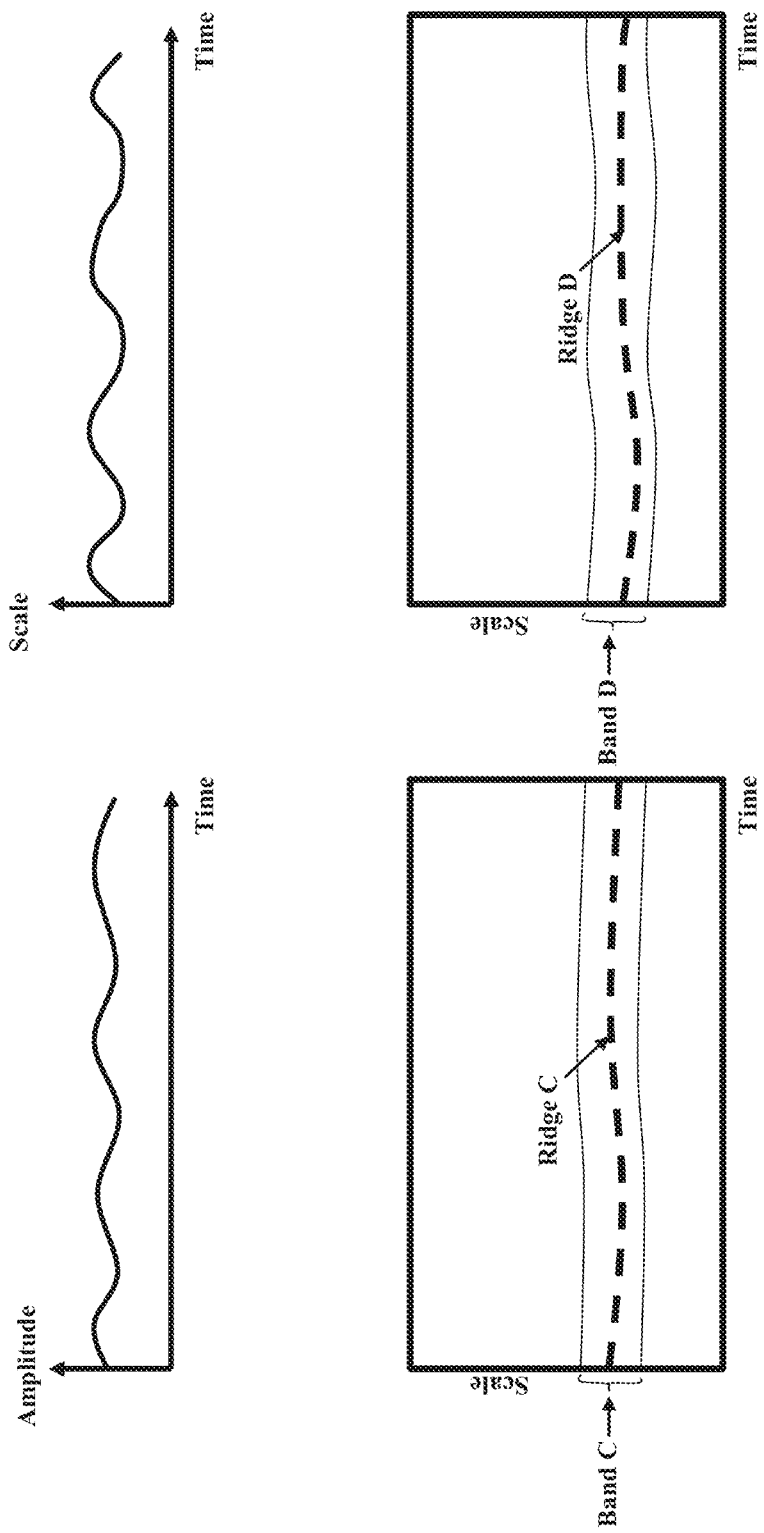
FIG. 3(d) shows an illustrative schematic of signals associated with a ridge in FIG. 3(c) and illustrative schematics of a farther wavelet decomposition of these newly derived signals in accordance with an embodiment.

As discussed above, pertinent repeating features in the signal give rise to a time-scale band in wavelet space or a resealed wavelet space. For a periodic signal, this band remains at a constant scale in the time-scale plane. For many real signals, especially biological signals, the band may be non-stationary; varying in scale, amplitude, or both over time. FIG. 3(c) shows an illustrative schematic of a wavelet transform of a signal containing two pertinent components leading to two bands in the transform space, according to an embodiment. These bands are labeled band A and band B on the three-dimensional schematic of the wavelet surface. In this embodiment, the band ridge is defined as the locus of the peak values of these bands with respect to scale. For purposes of discussion, it may be assumed that band B contains the signal information of interest. This will be referred to as the "primary band". In addition, it may be assumed that the system from which the signal originates, and from which the transform is subsequently derived, exhibits some form of coupling between the signal components in band A and band B. When noise or other erroneous features are present in the signal with similar spectral characteristics of the features of band B then the information within band B can become ambiguous (i.e., obscured, fragmented or missing). In this case, the ridge of band A may be followed in wavelet space and extracted either as an amplitude signal or a scale signal which will be referred to as the "ridge amplitude perturbation" (RAP) signal and the "ridge scale perturbation" (RSP) signal, respectively. The RAP and RSP signals may be extracted by projecting the ridge onto the time-amplitude or time-scale planes, respectively. The top plots of FIG. 3(d) show a schematic of the RAP and RSP signals associated with ridge A in FIG. 3(c). Below these RAP and RSP signals are schematics of a further wavelet decomposition of these newly derived signals. This secondary wavelet decomposition allows for information in the region of band B in FIG. 3(c) to be made available as band C and band D. The ridges of bands C and D may serve as instantaneous time-scale characteristic measures of the signal components causing bands C and D. This technique, which will be referred to herein as secondary wavelet feature decoupling (SWFD), may allow information concerning the nature of the signal components associated with the underlying physical process causing the primary band B (FIG. 3(c)) to be extracted when band B itself is obscured in the presence of noise or other erroneous signal features.

In some instances, an inverse continuous wavelet transform may be desired, such as when modifications to a scalogram (or modifications to the coefficients of a transformed signal) have been made in order to, for example, remove artifacts. In one embodiment, there is an inverse continuous wavelet transform which allows the original signal to be recovered from its wavelet transform by integrating over all scales and locations, a and b:

$$x(t) = \frac{1}{C_g} \int_{-\infty}^{\infty} \int_0^{\infty} T(a,b) \frac{1}{\sqrt{a}} \psi\left(\frac{t-b}{a}\right) \frac{da\,db}{a^2} \quad (8)$$

which may also be written as:

$$x(t) = \frac{1}{C_g} \int_{-\infty}^{\infty} \int_0^{\infty} T(a,b)\psi_{a,b}(t) \frac{da\,db}{a^2} \quad (9)$$

where $C_g$ is a scalar value known as the admissibility constant. It is wavelet type dependent and may be calculated from:

$$C_g = \int_0^{\infty} \frac{|\hat{\psi}(f)|^2}{f} df \quad (10)$$

Figure 3E:
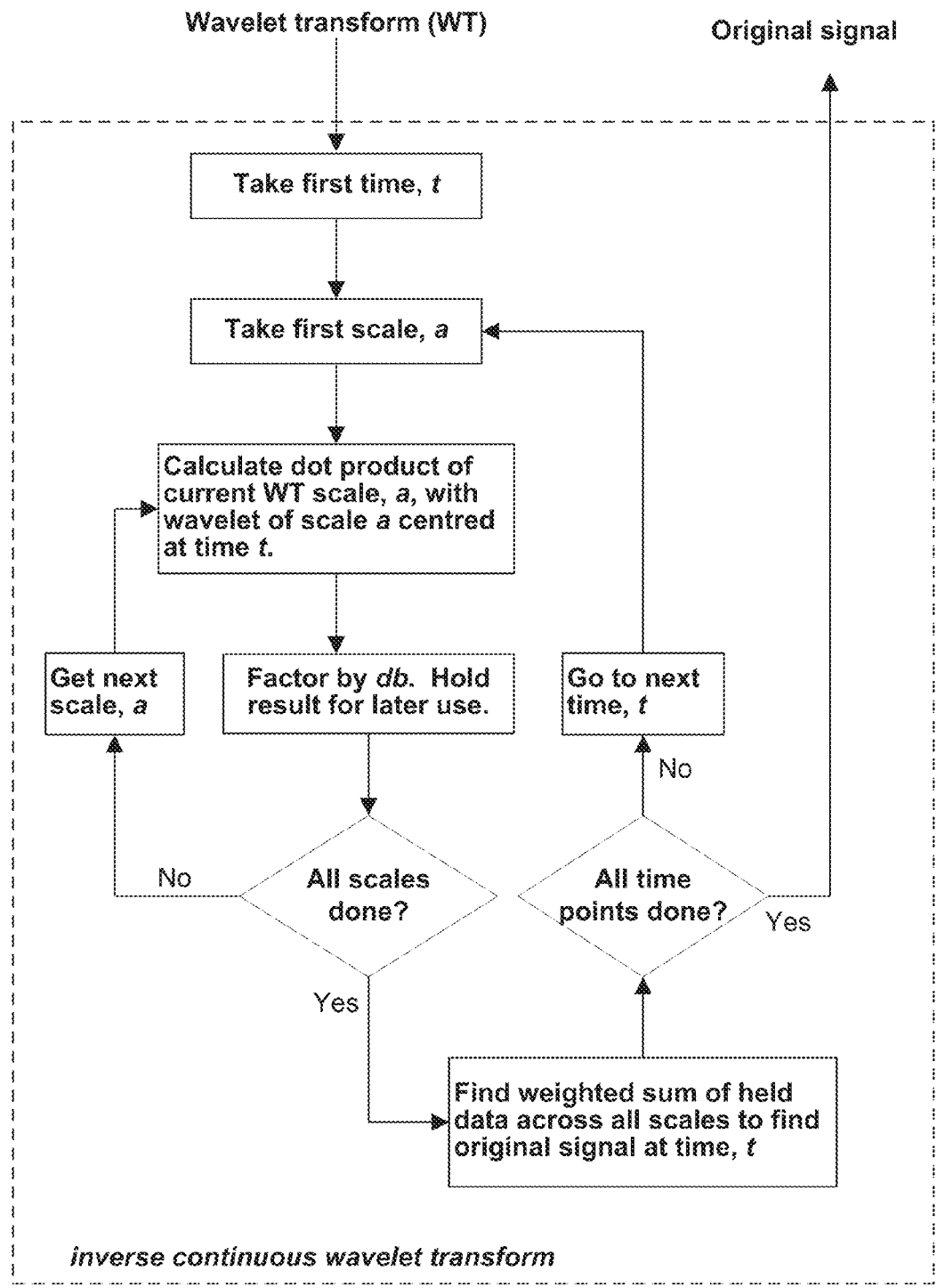
FIGS. 3(e) and 3(f) are flow charts of illustrative steps involved in performing an inverse continuous wavelet transform in accordance with embodiments.
Figure 3F:
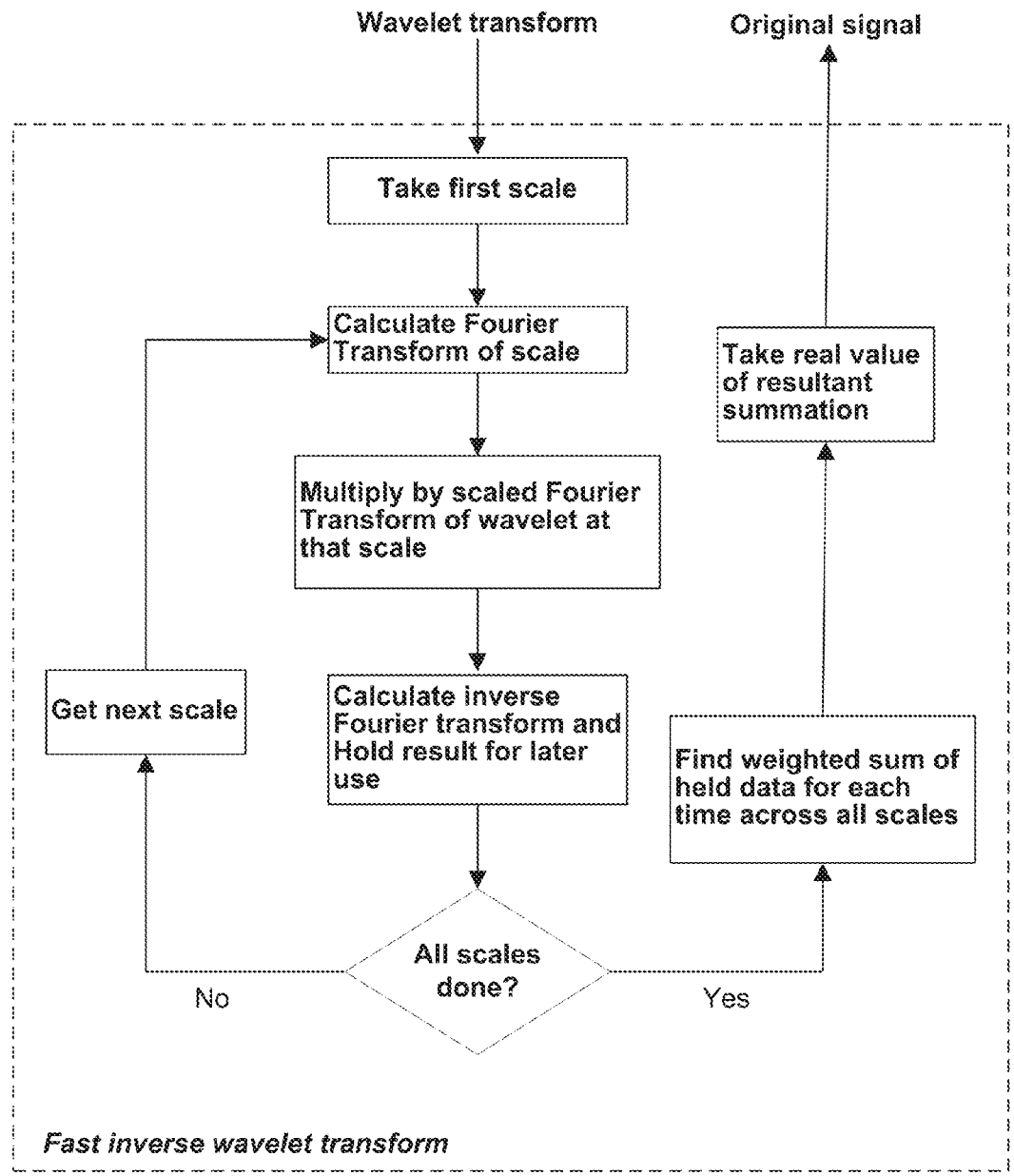

FIG. 3(e) is a flow chart of illustrative steps that may be taken to perform an inverse continuous wavelet transform in accordance with the above discussion. An approximation to the inverse transform may be made by considering equation (8) to be a series of convolutions across scales. It shall be understood that there is no complex conjugate here, unlike for the cross correlations of the forward transform. As well as integrating over all of a and b for each time t, this equation may also take advantage of the convolution theorem which allows the inverse wavelet transform to be executed using a series of multiplications. FIG. 3(f) is a flow chart of illustrative steps that may be taken to perform an approximation of an inverse continuous wavelet transform. It will be understood that any other suitable technique for performing an inverse continuous wavelet transform may be used in accordance with the present disclosure.

Figure 4:
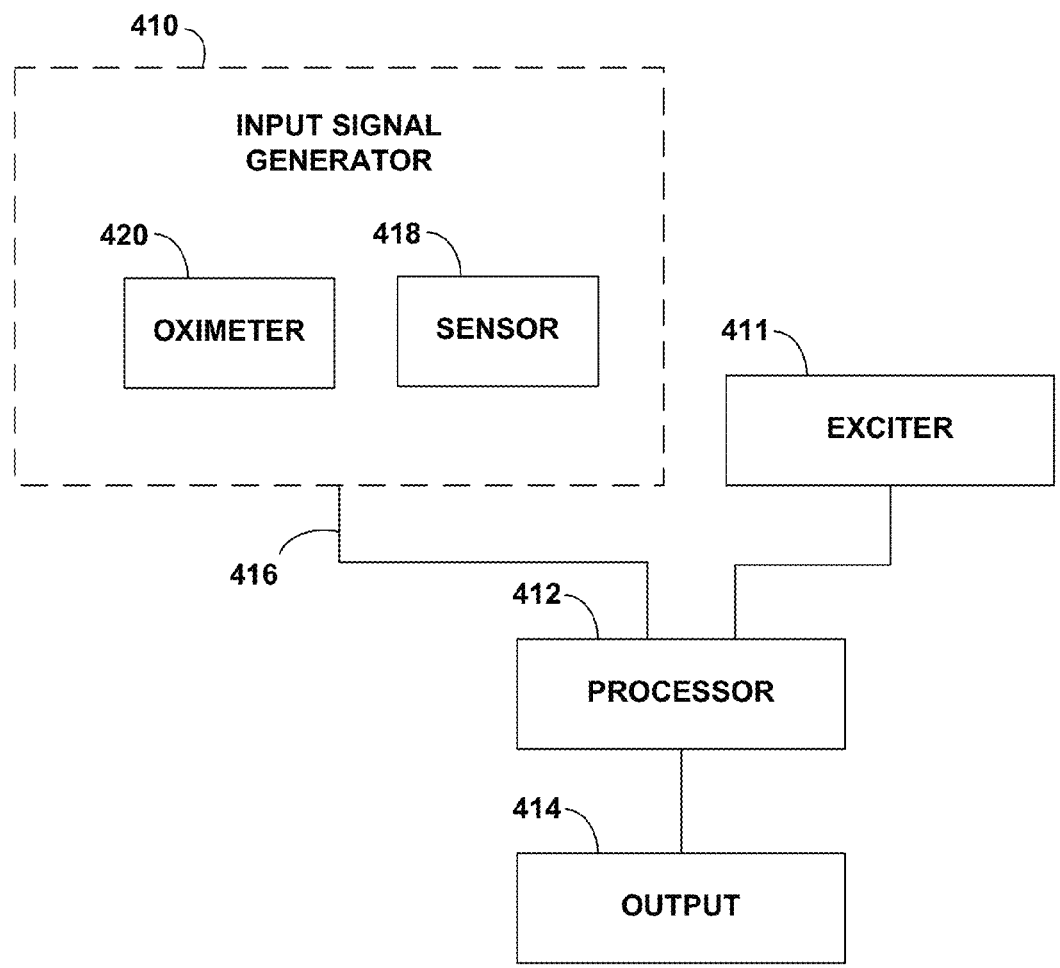
FIG. 4 is a block diagram of an illustrative continuous wavelet processing system in accordance with some embodiments.

FIG. 4 is an illustrative continuous wavelet processing system in accordance with an embodiment. In this embodiment, input signal generator 410 generates an input signal 416. As illustrated, input signal generator 410 may include oximeter 420 coupled to sensor 418, which may provide as input signal 416, a PPG signal. It will be understood that input signal generator 410 may include any suitable signal source, signal generating data, signal generating equipment, or any combination thereof to produce signal 416. Signal 416 may be any suitable signal or signals, such as, for example, biosignals (e.g., electrocardiogram, electroencephalogram, electrogastrogram, electromyogram, heart rate signals, pathological sounds, ultrasound, or any other suitable biosignal), dynamic signals, non-destructive testing signals, condition monitoring signals, fluid signals, geophysical signals, astronomical signals, electrical signals, financial signals including financial indices, sound and speech signals, chemical signals, meteorological signals including climate signals, and/or any other suitable signal, and/or any combination thereof. Processing system 400 may also include exciter 411 for inducing perturbations in a patient (see, e.g., exciter 13 (FIGS. 1 and 2)). Exciter 411 may be coupled to processor 412, and the processor may provide control signals to the exciter.

An oximeter may include a light sensor that is placed at a site on a patient, typically a fingertip, toe, forehead or earlobe, or in the case of a neonate, across a foot. The oximeter may pass light using a light source through blood perfused tissue and photoelectrically sense the absorption of light in the tissue. For example, the oximeter may measure the intensity of light that is received at the light sensor as a function of time. A signal representing light intensity versus time or a mathematical manipulation of this signal (e.g., a scaled version thereof, a log taken thereof, a scaled version of a log taken thereof, etc.) may be referred to as the photoplethysmograph (PPG) signal. In addition, the term "PPG signal," as used herein, may also refer to an absorption signal (i.e., representing the amount of light absorbed by the tissue) or any suitable mathematical manipulation thereof. The light intensity or the amount of light absorbed may then be used to calculate the amount of the blood constituent (e.g., oxyhemoglobin) being measured as well as the pulse rate and when each individual pulse occurs.

In this embodiment, signal 416 may be coupled to processor 412. Processor 412 may be any suitable software, firmware, and/or hardware, and/or combinations thereof for processing signal 416. For example, processor 412 may include one or more hardware processors (e.g., integrated circuits), one or more software modules, computer-readable media such as memory, firmware, or any combination thereof. Processor 412 may, for example, be a computer or may be one or more chips (i.e., integrated circuits). Processor 412 may perform the calculations associated with the continuous wavelet transforms of the present disclosure as well as the calculations associated with any suitable interrogations of the transforms. For example, processor 412 may determine the phase composition of a signal by analyzing a continuous wavelet transform of the signal and then use the phase composition of the signal to determine the patient's blood pressure. Processor 412 may perform any suitable signal processing of signal 416 to filter signal 416, such as any suitable band-pass filtering, adaptive filtering, closed-loop filtering, and/or any other suitable filtering, and/or any combination thereof.

Processor 412 may be coupled to one or more memory devices (not shown) or incorporate one or more memory devices such as any suitable volatile memory device (e.g., RAM, registers, etc.), non-volatile memory device (e.g., ROM, EPROM, magnetic storage device, optical storage device, flash memory, etc.), or both. The memory may be used by processor 412 to, for example, store data corresponding to a continuous wavelet transform of input signal 416, such as data representing a scalogram. In one embodiment, data representing a scalogram may be stored in RAM or memory internal to processor 412 as any suitable three-dimensional data structure such as a three-dimensional array that represents the scalogram as energy levels in a time-scale plane. Any other suitable data structure may be used to store data representing a scalogram. Processor 412 may be coupled to a calibration device (not shown) that may generate or receive as input reference blood pressure measurements for use in calibrating CNIBP calculations.

Processor 412 may be coupled to output 414. Output 414 may be any suitable output device such as, for example, one or more medical devices (e.g., a medical monitor that displays various physiological parameters, a medical alarm, or any other suitable medical device that either displays physiological parameters or uses the output of processor 412 as an input), one or more display devices (e.g., monitor, PDA, mobile phone, any other suitable display device, or any combination thereof), one or more audio devices, one or more memory devices (e.g., hard disk drive, flash memory, RAM, optical disk, any other suitable memory device, or any combination thereof), one or more printing devices, any other suitable output device, or any combination thereof.

It will be understood that system 400 may be incorporated into system 10 (FIGS. 1 and 2) in which, for example, input signal generator 410 may be implemented as parts of sensor 12 and monitor 14 and processor 412 may be implemented as part of monitor 14.

In one embodiment, portions of system 400 may be configured to be portable. For example, all or a part of system 400 may be embedded in a small, compact object carried with or attached to the patient (e.g., a watch (or other piece of jewelry) or cellular telephone). In such a portable embodiment, a wireless transceiver (not shown) may also be included in system 400 to enable wireless communication with other components of system 10. As such, system 10 may be part of a fully portable and continuous blood pressure monitoring solution.

According to the present disclosure, reliable blood pressure measurements may be derived from inducing perturbations and obtaining a PPG signal from a sensor or probe. In one embodiment, the constants a and b in equation (1) above may be determined by performing a calibration. The calibration may involve taking a reference blood pressure reading to obtain a reference blood pressure $P_0$, measuring the phase composition of the input signal to determine an elapsed time $T_0$ corresponding to the reference blood pressure, and then determining values for both of the constants a and b from the reference blood pressure and phase composition. Calibration may be performed at any suitable time (e.g., once initially after monitoring begins) or on any suitable schedule (e.g., a periodic or event-driven schedule).

In one embodiment, the calibration may include performing calculations mathematically equivalent to $$a = c_1 + \frac{c_2(P_0 - c_1)}{\ln(T_0) + c_2} \tag{11}$$

and $$b = \frac{P_0 - c_1}{\ln(T_0) + c_2} \tag{12}$$

to obtain values for the constants a and b, where $c_1$ and $c_2$ are predetermined constants that may be determined, for example, based on empirical data.

In another embodiment, determining the plurality of constants in equation (1) may include performing calculations mathematically equivalent to $$a = P_0 - (c_3 T_0 + c_4)\ln(T_0) \tag{13}$$

and $$b = c_3 T_0 + c_4 \tag{14}$$

where a and b are first and second constants and $c_3$ and $c_4$ are predetermined constants that may be determined, for example, based on empirical data.

In one embodiment, equation (1) may include a non-linear function which is monotonically decreasing and concave upward in a manner specified by the constants.

As mentioned above, equation (1) may be used to determine estimated blood pressure measurements from the phase composition of an input signal after a perturbation has been induced. In one embodiment, the PPG signal used in the CNIBP monitoring techniques described herein are generated by a pulse oximeter or similar device.

The present disclosure may be applied to measuring systolic blood pressure, diastolic blood pressure, mean arterial pressure (MAP), or any combination of the aforementioned blood pressures on an on-going, continuous, or periodic basis.

In one embodiment, measuring the time difference, T, may include comparing the phase composition of a detected signal at a sensor or probe location with the phase composition at an exciter location where perturbations are induced. Any differences between the detected signal at the sensor or probe location and the signal at the exciter location may be indicative of the effect that the patient's cardiovascular system had on the induced perturbation as it propagated through the patient's tissue. Accordingly, the phase composition of the detected signal at the sensor or probe location relative to exciter location may indicate the amount of time required for the induced perturbation to travel from the exciter (see, e.g., exciter 13 (FIGS. 1 and 2)) to a sensor or probe (see, e.g., sensor 12 (FIGS. 1 and 2)). The measured phase drift between the two signals may be used to generate a value for the time difference, T, in equation (1).

In one embodiment, the phase composition of the input perturbation signal may be used to determine detailed information about the patient's physiological parameters. For example, the phase composition of the input signal can be analyzed to determine information beyond merely the time difference, T. The phase composition of the input signal may include multiple phase measurements, and each phase measurement or combination of phase measurements may be analyzed to determine the effect of the patient's circulatory system on the propagation of the induced perturbation. For example, the continuous wavelet transform of an input signal may be calculated, and the phase component of each scale in the transform may be analyzed or compared to corresponding phase components in the continuous wavelet transform of a detected signal at the sensor or probe location. From this analysis, information about the patient's circulatory system may be determined.

Figure 5:
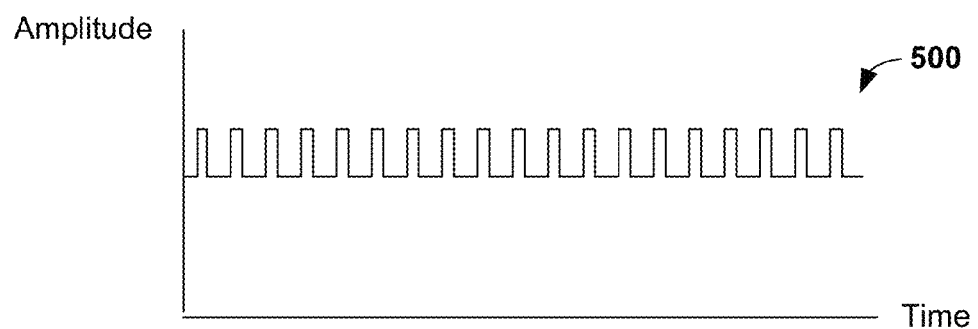
FIG. 5 shows an illustrative control signal in accordance with an embodiment.

FIG. 5 shows illustrative exciter control signal 500. An exciter (see, e.g., exciter 13 (FIGS. 1 and 2)) may induce perturbations in response to control signal 500. Control signal 500 may, for example, include relatively short electrical pulses that occur at a regular frequency. Each pulse may create a mechanical response in an exciter that induces a perturbation. Control signal 500 is merely illustrative and other signals may be used to induce perturbations in accordance with the disclosure. For example, a control signal may include a combination of electrical pulses. Providing a control signal with a particular combination of electrical pulses may create a distinct pattern in a PPG signal and therefore decrease the likelihood of overlooking or misidentifying a characteristic point in the PPG signal.

Figure 6:
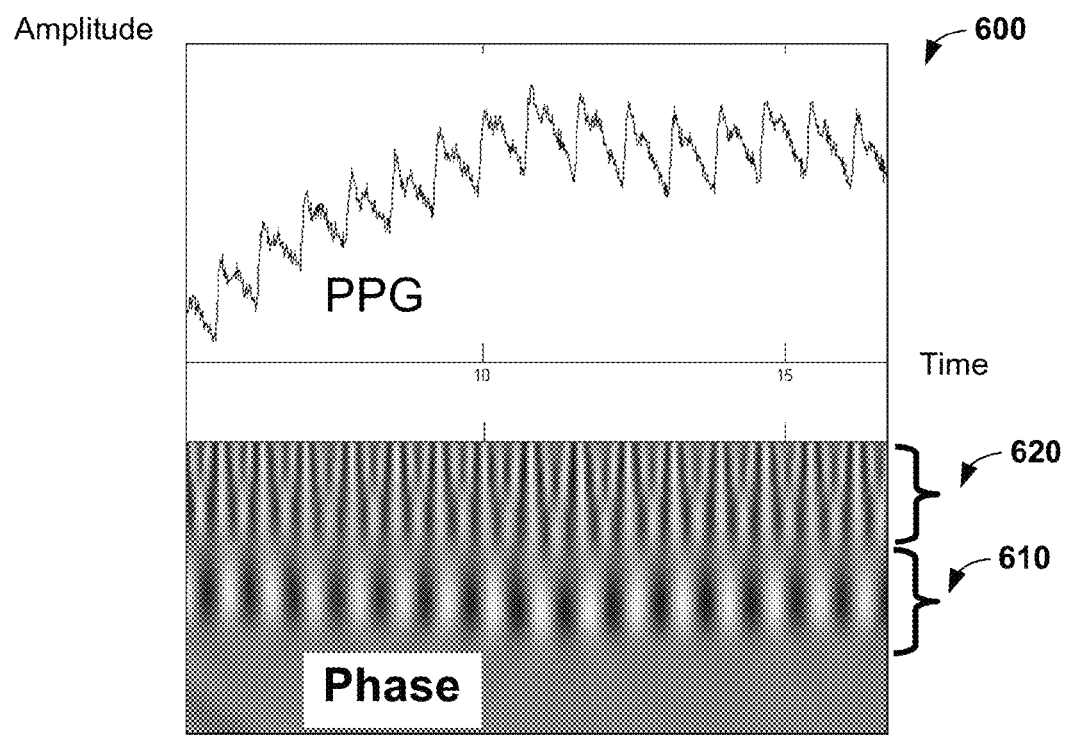
FIG. 6 shows an illustrative PPG signal in accordance with an embodiment.

FIG. 6 shows illustrative PPG signal 600. As described above, in one embodiment, PPG signal 600 may be generated by a pulse oximeter or similar device positioned at any suitable location of a subject's body. Signal 600 may be generated based on measurements taken by a sensor or probe (see, e.g., sensor 12 (FIGS. 1 and 2)) while an exciter (see, e.g., exciter 13 (FIGS. 1 and 2)) induces perturbations. For example, PPG signal 500 may be generated while an exciter induces perturbation based on control signal 500. Accordingly, PPG signal 600 may include both (1) the effects of the induced perturbations that were based on the known control signal and (2) any changes in the induced perturbation as it propagated through the patient's circulatory system. By comparing the continuous wavelet transform of PPG signal 600 to the continuous wavelet transform of a detected signal at the exciter location, one or more physiological parameters relating to the patient's circulatory system (e.g., blood pressure) may be measured.

FIG. 6 also includes the phase composition of PPG signal 600. The phase composition shown in FIG. 6 may be determined by generating the scalogram of PPG signal 600 and extracting the phase composition of the resulting scalogram. The phase from similar scales in the scalograms at the exciter and sensor or probe location may then be compared at similar times to yield clinically useful information.

The phase composition may include phase components in region 610 that correspond to the predominate scale of the induced perturbation. The phase components in region 610 may be generally indicative of the amount of time required for an induced perturbation to travel from an exciter (see, e.g., exciter 13 (FIGS. 1 and 2)) to a sensor or probe (see, e.g., sensor 12 (FIGS. 1 and 2)). As propagation time changes, so does the phase difference between the exciter signal and the detected PPG signal at the sensor or probe location. As such, the phase drift between scalograms generated at the exciter location and the sensor or probe location may be used as a proxy for pulse wave velocity (e.g., assuming a constant propagation length). This pulse wave velocity may then be used to compute the elapsed time, T, for use in question (1) (or in any other blood pressure equation using an elapsed time value between corresponding points of pulse signals). In one embodiment, a reference blood pressure measurement may be made and changes in the phase components in region 610 may be indicative of changes in the patient's blood pressure with respect to the reference blood pressure measurement.

The phase composition may include phase components in region 620 that correspond to smaller scales than region 610. The phase components in region 620 may, for example, be indicative of the dispersion and attenuation of the induced propagation in the patient's circulatory system. For example, dispersion may be determined by comparing how the scale values of highest energy change in the sensor or probe scalogram when compared to those same values of the exciter scalogram. The dominant scales may be expected to be lower, and the high values may spread over more scales due to dispersion. Likewise, the attenuation at different scales can be determined by finding how the relative amplitude at given scales changes (e.g., in terms of the ratio) between the exciter scalogram and sensor scalogram (e.g., relatively, the scales with higher characteristic frequencies may be expected to be attenuated more than those of a lower scale). Accordingly, the phase components in region 620 may be analyzed to provide more detailed information related to a patient's physiological parameters. In one embodiment, the phase components in region 620 may be used to determine physiological parameters other than blood pressure. For example, the phase components in region 620 may be used to determine detailed information about a patient's blood flow.

In accordance with the present disclosure, analyzing physiological parameters based on phase components derived from a continuous wavelet transform of an input signal may be advantageous over, for example, Fourier methods. For example, phase composition derived from a continuous wavelet transform may be calculated relative to (and weighted strongly to) a wavelet's position with respect to the input signal. Phase composition derived from Fourier methods, on the other hand, is typically calculated relative to the beginning of the input signal or a section of the input signal. Accordingly, instantaneous changes in phase may be more accurately calculated using a continuous wavelet transform, and the physiological measurements based on the phase calculations may also be more reliable and accurate.

A patient's blood pressure may be monitored continuously using a moving PPG signal. A PPG signal may be generated using, for example, a pulse oximeter (or other similar device) and associated hardware software, or both. While the PPG signal is being monitored, an exciter may continuously or periodically induce perturbations in the patient's body. A processor may then continuously analyze the PPG signal in order to continuously monitor a patient's blood pressure.

In one embodiment, past blood pressure measurements may be used to refine current and future measurements. For example, to avoid large swings in detected blood pressure a running or moving blood pressure average may be maintained. In one embodiment, detected blood pressure values outside some pre-defined threshold, based on, for example, a moving average may be ignored. Additionally or alternatively, detected blood pressure values outside some pre-defined threshold, based on, for example, a moving average may automatically signal a recalibration event.

According to one embodiment, one or more calibration (or recalibration) steps may be employed by measuring the patient's blood pressure (or a reference blood pressure), $P_0$, and then measuring the corresponding phase composition of the PPG signal. Updated or refined values for constants a and b of equation (1) (or other suitable blood pressure equation) may then be computed based on the calibration. Calibration may be performed once, initially at the start of the continuous monitoring, or calibration may be performed on a regular or event-driven schedule.

Figure 7:
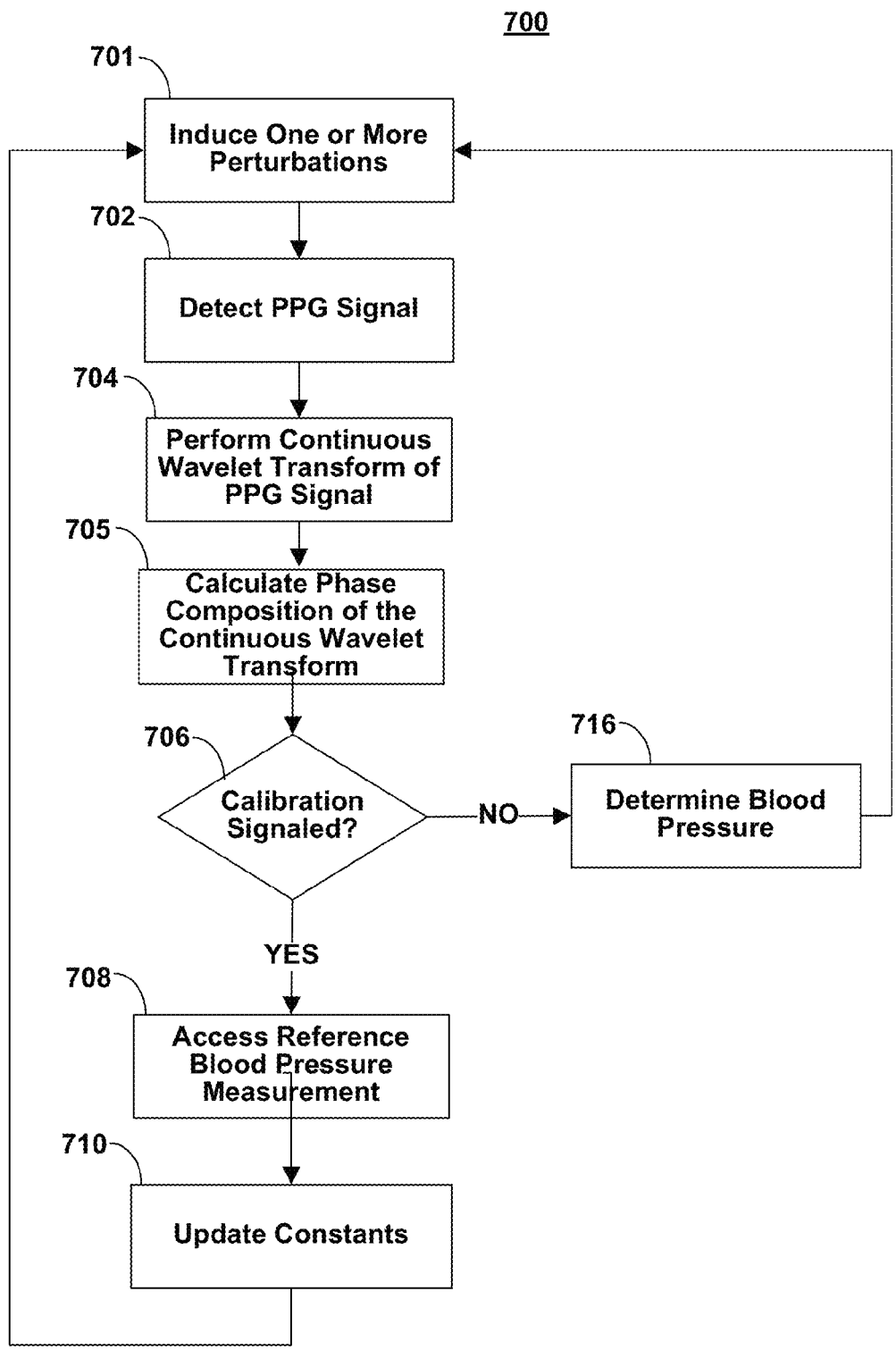
FIG. 7 is a flow chart of illustrative steps for determining blood pressure in accordance with an embodiment.

FIG. 7 shows illustrative process 700 for determining blood pressure. At step 701, one or more perturbations may be induced in a patient. For example, exciter 13 (FIGS. 1 and 2) may induce one or more perturbations in a patient. At step 702, a PPG signal may be detected from a patient. For example, monitor 14 (FIGS. 1 and 2) may be used to detect a PPG signal from patient 40 (FIG. 2) using, for example, sensor 12 (FIGS. 1 and 2). Any sensor or probe used to detect a PPG signal at step 702 may be located close to or even on the same appendage as an exciter used to induce a perturbation in step 701.

At step 704, a continuous wavelet transform of the PPG signal may be calculated. For example, microprocessor 48 (FIG. 2) may calculate a continuous wavelet transform of the PPG signal. Microprocessor 48 (FIG. 2) may calculate a continuous wavelet transform using any suitable signal processing techniques.

For example, microprocessor 48 (FIG. 2) and/or processor 312 (FIG. 3) may implement various types of digital or analog filtering, using, for example, low pass and band-pass filters in order to preprocess the PPG signal before calculating a continuous wavelet transform of the PPG signal. In one embodiment, to improve results, the PPG signal is first filtered using a low pass or band-pass filter before any continuous wavelet transform is calculated. The signal may be filtered one or more times using any combination of filters.

At step 705, a phase composition of the continuous wavelet transform may be calculated. For example, microprocessor 48 (FIG. 2) may calculate the phase composition of the continuous wavelet transform or scalogram of the detected PPG signal. In one embodiment, the phase composition may be calculated relative to the phase composition of the control signal used to induce one or more perturbations in step 701. For example, a phase drift between may be computed between a scalogram generated at the exciter location and a scalogram generated at the sensor or probe location by comparing phase from similar scales of the scalograms at similar times. In an embodiment, the phase at scales of characteristic frequency close to the exciter frequency are analyzed.

After the phase composition is calculated, at step 706 a determination is made whether a calibration has been signaled (or should be signaled). As described above, calibration may be performed once after monitoring initialization or calibration may be performed periodically on any suitable schedule. For example, a calibration event may be signaled by microprocessor 48 (FIG. 2) after blood pressure measurements have exceeded some predefined threshold window or some standard deviation from the mean or moving average of previous measurements. As another example, a calibration event may be signaled by microprocessor 48 (FIG. 2) after the passage of some predetermined length of time from the last calibration event. For example, microprocessor 48 (FIG. 2) may access a timer or clock and automatically signal calibration events on a periodic schedule.

If calibration has been signaled, at step 708 one or more reference blood pressure measurements may be accessed. For example, calibration device 80 (FIGS. 1 and 2) may continuously or periodically generate reference blood pressure measurements for use in calibration. These reference blood pressure measurements may be derived from any suitable invasive or non-invasive blood pressure monitoring technique. The measurements may also be accessed from any suitable storage device, or the measurements may be manually inputted by an operator (e.g., if read from an external monitoring or measurement device).

After the reference blood pressure measurement or measurements are accessed, at step 710 constant parameters may be updated. For example, one or more of constants a and b of equation (1) above may be updated. In other embodiments, any other suitable constants or parameters (of any other suitable blood pressure equation) may be updated at step 710.

In one embodiment, a determination may be made at step 710 whether or not to change the control signal and therefore the induced perturbations. For example, the control signal may be altered to include particular components that may be more easily identified in the phase composition of the PPG signal.

In one embodiment, perturbations may be induced based on a variety of control signals and the control signal which yielded the closest blood pressure measurement to the reference blood pressure measurement accessed at step 708 may be selected as the new control signal.

After step 710, process 700 may return to step 701. For example, once the constants are updated, process 700 may continue by inducing one or more perturbations.

If the determination made at step 706 indicates that calibration is not necessary, process 700 may proceed with step 716. At step 716, the patient's blood pressure may be determined. In some embodiments, microprocessor 48 (FIG. 2) may determine the patient's blood pressure. The patient's blood pressure may be determined based, at least in path on the phase composition of the PPG signal (or the scalogram of the PPG signal). For example, the blood pressure may be determined by analyzing the phase composition of the PPG signal at a sensor or probe location relative to the control signal used to induce perturbations, and then using the phase composition to calculate the time required for the induced perturbations to propagate through the patient's circulatory system. This time can then be used as the time difference, T, in equation (1) above (or any other blood pressure equation using an elapsed time between the arrival of corresponding points of a pulse signal) to compute estimated blood pressure measurements in accordance with the present disclosure. In some embodiments, the patient's blood pressure may be determined by analyzing a previous blood pressure measurement along with any changes in the phase composition of the PPG signal.

After a blood pressure measurement is determined at step 716, process 700 may return to step 701 and induce new perturbations. As such, process 700 may generate blood pressure measurements continuously. Phase differences between the exciter location and the sensor or probe location may then be monitored continuously. Changes in phase should vary slowly over time with changes in blood pressure.

After blood pressure measurements are determined, the measurements may be outputted, stored, or displayed in any suitable fashion. For example, multi-parameter patient monitor 26 (FIG. 1) may display a patient's blood pressure on display 28 (FIG. 1). Additionally or alternatively, the measurements may be saved to memory or a storage device (e.g., ROM 52 or RAM 54 of monitor 14 (FIG. 2)) for later analysis or as a log of a patient's medical history.

In practice, one or more steps shown in process 700 may be combined with other steps, performed in any suitable order, performed in parallel (e.g., simultaneously or substantially simultaneously), or removed.

The foregoing is merely illustrative of the principles of this disclosure and various modifications can be made by those skilled in the art without departing from the scope and spirit of the disclosure. The above described embodiments are presented for purposes of illustration and not of limitation. The present disclosure also can take many forms other than those explicitly described herein. Accordingly, it is emphasized that the disclosure is not limited to the explicitly disclosed methods, systems, and apparatuses, but is intended to include variations to and modifications thereof which are within the spirit of the following claims.

What is claimed is:

1. A method for monitoring blood pressure comprising:
inducing a perturbation signal in a subject's body;
detecting a signal from the subject's body;
transforming the detected signal using a continuous wavelet transform to generate a scalogram, wherein the scalogram comprises three dimensional data, wherein a first dimension of the scalogram corresponds to time, wherein a second dimension of the scalogram corresponds to scale, and wherein a third dimension of the scalogram corresponds to phase;

determining, from the scalogram, a phase that corresponds to a particular time and scale;

determining, based at least in part on the phase and the perturbation signal, a phase difference; and determining, based at least in part on the determined phase difference, a blood pressure measurement.

2. The method of claim 1 wherein determining the phase difference comprises:

generating a scalogram of the induced perturbation signal; and comparing the scalogram of the detected signal and the scalogram of the induced perturbation signal.

3. The method of claim 2 wherein comparing the scalogram of the detected signal and the scalogram of the induced perturbation signal comprises comparing phase information from the same or similar scales at the same or similar times of the scalogram of the detected signal and the scalogram of the induced perturbation signal.

4. The method of claim 3 wherein the same or similar scales of the first and second scalograms comprises at least one scale at the characteristic frequency of the induced perturbation signal.

5. The method of claim 1 wherein determining a blood pressure measurement comprises determining an elapsed time for the induced perturbation signal to propagate a fixed distance.

6. The method of claim 5 wherein determining a blood pressure measurement comprises taking the natural log of the elapsed time.

7. The method of claim 1 wherein determining a blood pressure measurement comprises determining a time difference, T, based at least in part on the determined phase difference and solving a multi-parameter equation that includes the time difference.

8. The method of claim 7 wherein the multi-parameter equation is $$p = a + b \cdot \ln(T)$$

or a mathematical equivalent thereof, where p is the determined blood pressure measurement and a and b are constants.

9. The method of claim 1 further comprising performing at least one calibration of the blood pressure measurement, the calibration based at least in part on a known reference blood pressure measurement.

10. The method of claim 1 wherein inducing a perturbation signal in a subject's body comprises inducing a known perturbation signal in the subject's body using an ultrasonic, acoustic, or mechanical exciter.

11. The method of claim 1 wherein detecting a signal from the subject's body comprises detecting a photoplethysmograph (PPG) signal from the subject's body.

12. A system for monitoring blood pressure comprising:
an exciter capable of inducing a perturbation signal in a subject's body;
a sensor capable of generating a detected signal from the subject's body; and
a processor capable of:
transforming the detected signal using a continuous wavelet to generate a scalogram, wherein the scalogram comprises three dimensional data, wherein a first dimension of the scalogram corresponds to time, wherein a second dimension of the scalogram corresponds to scale, and wherein a third dimension of the scalogram corresponds to phase;

determining, from the scalogram, a phase that corresponds to a particular time and scale;

determining, based at least in part on the phase and the perturbation signal, a phase difference; and determining, based at least in part on the determined phase difference, a blood pressure measurement.

13. The system of claim 12 wherein the processor is capable of determining the phase difference by:
generating a scalogram of the induced perturbation signal; and
comparing the scalogram of the detected signal and the scalogram of the induced perturbation signal.

14. The system of claim 13 wherein comparing the scalogram of the detected signal and the scalogram of the induced perturbation signal comprises comparing phase information from the same or similar scales at the same or similar times of the scalogram of the detected signal and the scalogram of the induced perturbation signal.

15. The system of claim 14 wherein the same or similar scales of the first and second scalograms comprises at least one scale at the characteristic frequency of the induced perturbation signal.

16. The system of claim 12 wherein the processor is capable of determining a blood pressure measurement by determining an elapsed time for the induced perturbation signal to propagate a fixed distance.

17. The system of claim 16 wherein the processor is capable of determining a blood pressure measurement by taking the natural log of the elapsed time.

18. The system of claim 12 wherein the processor is capable of determining a blood pressure measurement by determining a time difference, T, based at least in part on the determined phase difference and solving a multi-parameter equation that includes the time difference.

19. The system of claim 18 wherein the multi-parameter equation is $$p = a + b \cdot \ln(T)$$

or a mathematical equivalent thereof, where p is the determined blood pressure measurement and a and b are constants.

20. The system of claim 12 wherein the processor is capable of performing at least one calibration of the blood pressure measurement, the calibration based at least in part on a known reference blood pressure measurement.

21. The system of claim 12 wherein the exciter is capable of inducing a known perturbation signal in the subjects body using an ultrasonic, acoustic, or mechanical exciter.

22. The system of claim 12, wherein the sensor capable of generating a detected signal from the subject's body comprises a sensor capable of generating a photoplethysmograph (PPG) signal from the subject's body.

23. A non-transitory computer-readable medium for use in detecting an artifact in a signal, the computer-readable medium having computer program instructions recorded thereon for:
inducing a perturbation signal in a subject's body;
detecting a signal from the subject's body;
transforming the detected signal using a continuous wavelet transform to generate a scalogram, wherein the scalogram comprises three dimensional data, wherein a first dimension of the scalogram corresponds to time, wherein a second dimension of the scalogram corresponds to scale, and wherein a third dimension of the scalogram corresponds to phase;
determining, from the scalogram, a phase that corresponds to a particular time and scale;

determining, based at least in part on the phase and the perturbation signal, a phase difference; and determining, based at least in part on the determined phase difference, a blood pressure measurement.

* * * * *